(12) United States Patent
Ofer

(10) Patent No.: US 12,171,567 B2
(45) Date of Patent: *Dec. 24, 2024

(54) METHODS AND SYSTEMS FOR DISPLAYING EYE IMAGES TO SUBJECTS AND FOR INTERACTING WITH VIRTUAL OBJECTS

(71) Applicant: Moshe Ofer, Ramat Hasharon (IL)

(72) Inventor: Moshe Ofer, Ramat Hasharon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/114,999

(22) Filed: Feb. 28, 2023

(65) Prior Publication Data

US 2023/0200715 A1    Jun. 29, 2023

Related U.S. Application Data

(63) Continuation of application No. 17/968,907, filed on Oct. 19, 2022, now Pat. No. 11,660,040, which is a (Continued)

(51) Int. Cl.
*A61B 5/00*     (2006.01)
*A61B 5/378*    (2021.01)

(52) U.S. Cl.
CPC ............ *A61B 5/4064* (2013.01); *A61B 5/378* (2021.01); *A61B 5/4047* (2013.01); *A61B 5/4076* (2013.01); *A61B 5/6868* (2013.01)

(58) Field of Classification Search
CPC ..... A61B 5/4064; A61B 5/378; A61B 5/4047; A61B 5/4076; A61B 5/6868; A61B 5/291; A61B 5/398; A61B 5/375; A61B 5/16; A61B 5/369; A61N 1/0456; A61N 1/36025; A61H 2205/024; A61H 2230/10

See application file for complete search history.

(56) References Cited

U.S. PATENT DOCUMENTS

| 5,178,161 A | 1/1993 | Kovacs |
| 6,175,767 B1 | 1/2001 | Doyle, Sr. |

(Continued)

FOREIGN PATENT DOCUMENTS

| CN | 103705229 A | 4/2014 |
| CN | 204520668 U | 8/2015 |

(Continued)

OTHER PUBLICATIONS

International Search Report for PCT/IB2022/055761 Mailed on Nov. 30, 2022.

(Continued)

*Primary Examiner* — Patrick Fernandes
(74) *Attorney, Agent, or Firm* — Rivka Friedman

(57) ABSTRACT

A processing subsystem generates perceived images from information bearing nerve impulses that are transmitted from a subject's eye(s) to a visual processing region of the subject's brain along one or more nerves in response to the subject viewing a real-world scene. The processing subsystem generates display images based on the perceived images, and controls a display device to display the display images to the subject. In certain embodiments, the processing subsystem generates the display images by manipulating or modifying the perceived images to include virtual images, and provides a type of virtual pointing on the display images that is used to invoke one or more actions.

20 Claims, 3 Drawing Sheets

Related U.S. Application Data continuation-in-part of application No. 17/740,425, filed on May 10, 2022, now Pat. No. 11,712,191, which is a continuation of application No. 17/534,622, filed on Nov. 24, 2021, now Pat. No. 11,395,620.

(60) Provisional application No. 63/196,274, filed on Jun. 3, 2021.

(56) References Cited

U.S. PATENT DOCUMENTS

| | | |
|---|---|---|
| 6,728,578 B1 | 4/2004 | Voelkel |
| 7,991,475 B1 | 8/2011 | Tang |
| 8,369,958 B2 | 2/2013 | Kwon et al. |
| 9,327,120 B2 | 5/2016 | Richter et al. |
| 9,451,883 B2 | 9/2016 | Gallant et al. |
| 9,480,582 B2 | 11/2016 | Lundborg |
| 10,123,133 B2 | 11/2018 | Pontoppidan |
| 10,264,990 B2 | 4/2019 | Pasley et al. |
| 10,441,172 B2 | 10/2019 | Tanaka et al. |
| 10,925,509 B2 | 2/2021 | Nestor et al. |
| 11,071,465 B2 | 7/2021 | Angle et al. |
| 11,373,672 B2 | 6/2022 | Mesgarani et al. |
| 11,395,620 B1 | 7/2022 | Moshe |
| 11,467,665 B2 | 10/2022 | Gribetz |
| 2004/0155112 A1 | 8/2004 | Matsuda |
| 2004/0172098 A1 | 9/2004 | Greenberg et al. |
| 2005/0283202 A1 | 12/2005 | Gellman |
| 2008/0161915 A1 | 7/2008 | Ren |
| 2008/0242950 A1 | 10/2008 | Jung et al. |
| 2008/0319276 A1 | 12/2008 | Jung et al. |
| 2009/0216091 A1 | 8/2009 | Arndt |
| 2010/0026798 A1 | 2/2010 | Schmid |
| 2011/0144471 A1 | 6/2011 | Hsu et al. |
| 2011/0227586 A1 | 9/2011 | Lovetri et al. |
| 2013/0131537 A1 | 5/2013 | Tam |
| 2013/0184558 A1 | 7/2013 | Gallant et al. |
| 2014/0214120 A1 | 7/2014 | Simon et al. |
| 2014/0267401 A1 | 9/2014 | Urbach |
| 2015/0119689 A1 | 4/2015 | Pascual-Leone et al. |
| 2015/0142082 A1 | 5/2015 | Simon et al. |
| 2015/0248470 A1 | 9/2015 | Coleman et al. |
| 2016/0073887 A1 | 3/2016 | Lee et al. |
| 2016/0103487 A1 | 4/2016 | Crawford et al. |
| 2016/0109851 A1 | 4/2016 | Tsang |
| 2017/0087367 A1 | 3/2017 | Weisend |
| 2018/0021579 A1 | 1/2018 | Kahana et al. |
| 2018/0200389 A1 | 7/2018 | Wong et al. |
| 2018/0245097 A1 | 8/2018 | Vogel |
| 2018/0304095 A1 | 10/2018 | Register et al. |
| 2019/0082990 A1 | 3/2019 | Poltorak |
| 2019/0227490 A1 | 7/2019 | Waller et al. |
| 2019/0336060 A1 | 11/2019 | Shen et al. |
| 2019/0357797 A1 | 11/2019 | Nestor et al. |
| 2020/0187841 A1 | 6/2020 | Ayyad |
| 2020/0196932 A1 | 6/2020 | Johnson et al. |
| 2021/0293714 A1 | 9/2021 | Matoba et al. |
| 2022/0248148 A1 | 8/2022 | Verhulst et al. |
| 2022/0417678 A1 | 12/2022 | Moshe |

FOREIGN PATENT DOCUMENTS

| | | |
|---|---|---|
| WO | 2019235458 A1 | 12/2019 |
| WO | 2020242888 A1 | 12/2020 |

OTHER PUBLICATIONS

Robert Sanders, "Editing brain activity with holography," Apr. 30, 2018, Berkeley News (Year: 2018).

Pan Wang et al: "Verifying Design through Generative Visualization of Neural Activities", arxiv.org, Cornell University Library, 201 Olin Library Cornell University Ithaca, NY, 14853, Mar. 28, 2021 (Mar. 28, 2021) XP081918295.

Akashi Wataru et al: "Vowel Sound Synthesis from Electroencephalography during Listening and Recalling", Advanced Intelligent Systems, vol. 3, No. 2, Jan. 7, 2021 (Jan. 7, 2021) pp. 2000164, XO055881025, DE ISSN: 2640-4567, DOI: 10.1002/aisy.202000164.

Niketeghad Soroush et al: "Brain Machine Interfaces for Vision Restoration: The Current State of Cortical Visual Prosthetics", Neurotherapeutics, Springer International Publishing, Cham, vol. 16, No. 1, Sep. 7, 2018 (Sep. 7, 2018), pp. 134-143, XP036880191, ISSN: 1933-7213, DOI: 10.1007/S13311-018-0660-1.

Peter Zu Eulenburg et al: "On the recall of vestibular sensations", Brain Structure and Fuction, Springer, Berlin, DE, vol. 218, No. 1, Feb. 25, 2012 (Feb. 25, 2012), pp. 255-267, XP035156789, ISSN: 1863-2661, DOI: 10.1007/S00429-012-0399-0.

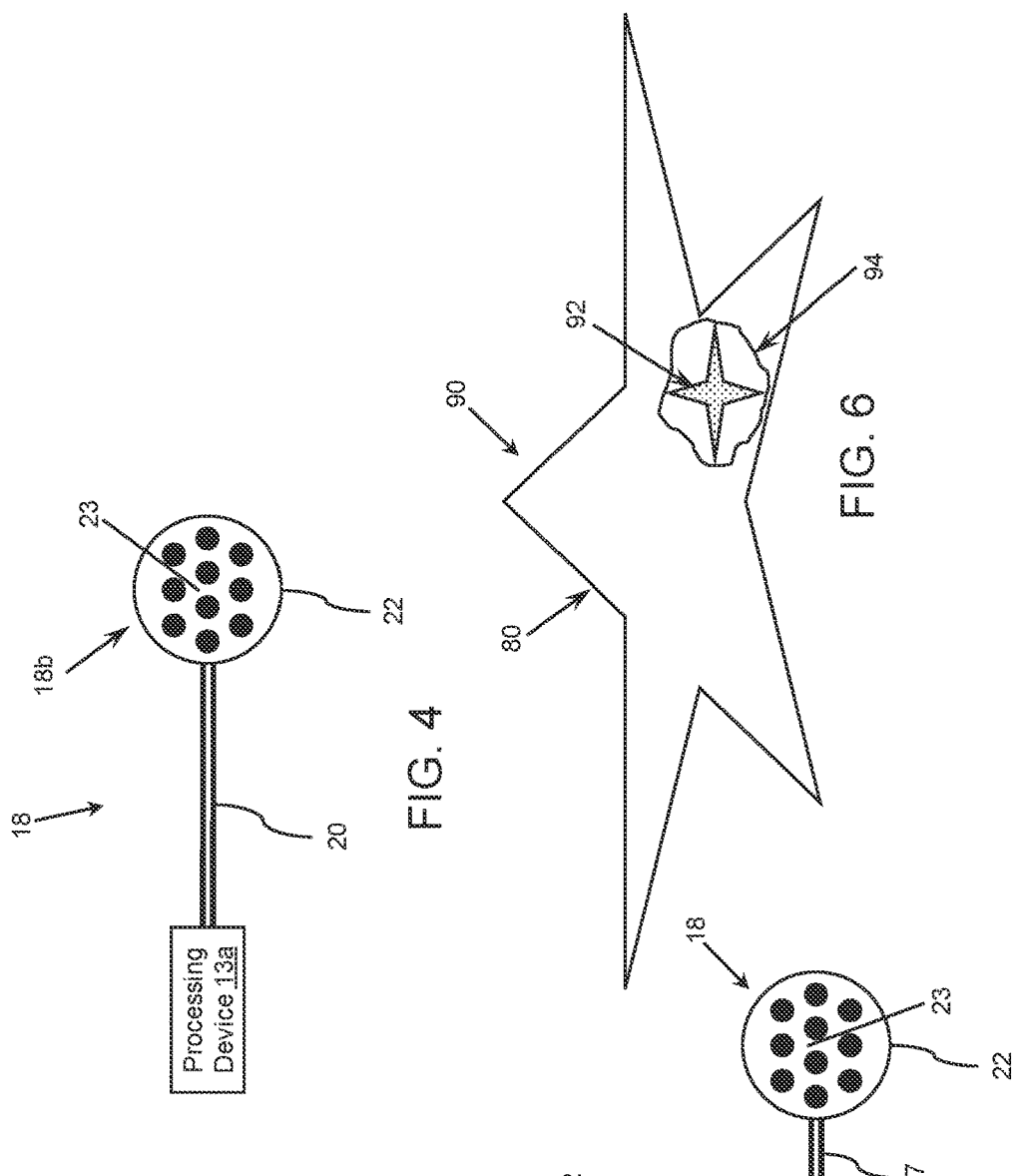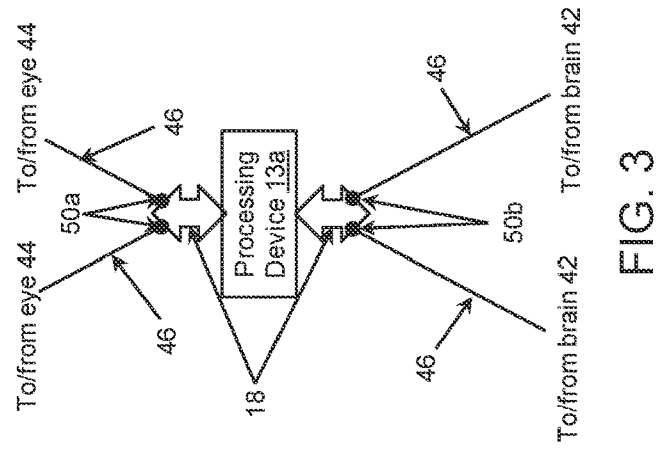

METHODS AND SYSTEMS FOR DISPLAYING EYE IMAGES TO SUBJECTS AND FOR INTERACTING WITH VIRTUAL OBJECTS

CROSS-REFERENCE TO RELATED APPLICATIONS

This application is a continuation of U.S. patent application Ser. No. 17/968,907, filed 19 Oct. 2022, which is continuation-in-part of U.S. patent application Ser. No. 17/740,425, filed May 10, 2022, which is a continuation of U.S. patent application Ser. No. 17/534,622, filed Nov. 24, 2021, now U.S. Pat. No. 11,395,620, which claims priority from U.S. Provisional Patent Application No. 63/196,274, filed Jun. 2, 2021, all disclosures of which are incorporated by reference in their entireties herein.

TECHNICAL FIELD

The present disclosure relates to displaying eye images based on conversion between image information bearing nerve impulses and image data.

BACKGROUND OF THE INVENTION

The human vision system comprises the eyes, the brain, and parts of the nervous system. In general, light is sensed by photoreceptors (rods and cones) in the eye, and is converted into nerve impulses that are transmitted to the brain by the optic nerve, to be interpreted by the brain as sight and vision.

SUMMARY OF THE INVENTION

Embodiments of the present invention provide systems and methods for displaying images to subjects. The displayed images are based on images that are generated from nerve impulses, carrying image information, that are transmitted from the eye(s) to the visual processing region of the subject's brain along one or more nerves in response to the subject viewing a real-world scene. The images that are generated from the nerve impulses are referred to as "perceived images" or "eye images". These eye images serve as the basis for the images that are displayed to the subject, and can, in certain embodiments, be manipulated and/or modified to include virtual images. In certain embodiments, the systems and methods provide a type of "virtual pointing" on the eye images or manipulated/modified eye images, which can be used to invoke one or more actions.

Certain preferred embodiments according to a first aspect of the present invention provide a processing subsystem that is communicatively coupled to a display device that can be deployed relative to a subject (i.e., user), for example between the eyes of the subject and a scene. The processing subsystem is operative to receive signals associated with nerve impulses transmitted to the visual processing region of the subject's brain by a nerve or nerves associated with the eye or eyes in response to the eye(s) viewing the scene during a sample period. The processing subsystem processes the received signals to generate a perceived image so as to convert the nerve impulses to the generated perceived image, whereby the perceived image is representative of a visual perception of the scene by the visual processing region (e.g., visual cortex) of the subject's brain. The processing subsystem is further operative to provide to the display device a display image, that is based on the generated perceived image, for display during a display period. In certain preferred but non-limiting embodiments, the processing subsystem is further operative to controllably and repeatedly switch the display device between a display mode associated with the display period and a non-display mode associated with the sample period so that the subject's view alternates between the display image (projected by the display device) and the scene.

Certain preferred embodiments according to a second aspect of the present invention provide a processing subsystem and a display device similar to as described above, however the processing subsystem is operative to generate the display image by modifying the perceived image with an image of an object such that the object appears as overlaid on the scene in the display image, and to identify a data marker or data object that mark/tag/identify one or more data elements in the display image that correspond to a spatial location of the object in the display image. For example, the processing subsystem is preferably operative to identify a data record (for example in a database) that has metadata associated with one or more data elements of image data of the display image, whereby the one or more data elements are associated with a spatial location of a portion of the display image that contains the object (or at least part of the object). In certain preferred but non-limiting embodiments, the processing subsystem is further operative to initiate or invoke a responsive action associated with the object in response to identifying the data record, for example when the data record includes a "trigger" (to initiate a responsive action) that is associated with the spatial location. In certain preferred but non-limiting embodiments, the processing subsystem identifies the data record in response to an action, initiated by the subject, on the portion of the display image that contains the object.

It should be noted that the two aspects of the present invention presented herein are of independent utility, such that the display mode switching is not limited to use in embodiments that perform data record identification. Similarly, the data record identification embodiments are not limited to use with embodiments that perform display mode switching. Nevertheless, there may be a particular synergy to an implementation which employs the two aforementioned aspects of the present invention together. It is further noted that the present invention may include additional aspects beyond the two aspects explicitly mentioned above, and that the present invention should not be limited to only these two aspects.

According to the teachings of an embodiment of the present invention, there is provided a system for use with a subject having a brain that includes a region responsible for visual perception. The system comprises: a display device operable in a display mode and a non-display mode; and a processing subsystem for communicating with at least one nerve associated with an eye of the subject, the processing subsystem configured to: receive signals associated with nerve impulses transmitted by the at least one nerve in response to viewing at least a portion of a scene by the eye during a sample period, the sample period coinciding with operation of the display device in the non-display mode, process the received signals to generate a perceived image representative of a visual perception of the scene by the region of the brain, and provide to the display device an image for display during a display period that coincides with operation of the display device in the display mode, the image being based on the perceived image.

Optionally, the processing subsystem is further configured to switch the display device between the non-display mode and the display mode, and the display device does not display images when operating in the non-display mode.

Optionally, the display device is an at least partially transparent display such that when the display device operates in the non-display mode at least a portion of the scene is viewable to the eye through the display device.

Optionally, when the display device operates in the display mode the display device displays images so as to be viewable by the eye, and when the display device operates in the non-display mode the display device does not display images.

Optionally, the display device is configured to operate in the non-display mode during a plurality of sampling periods and to operate in the display mode during a plurality of display periods.

Optionally, the processing subsystem is further configured to controllably switch the display device so that the display device alternates between operation in the non-display mode and operation in the display mode, and when the display device operates in the non-display mode the processing subsystem is configured to receive signals associated with nerve impulses transmitted by the at least one nerve in response to viewing at least a portion of the scene by the eye during a corresponding one of the sample periods, and when the display device operates in the display mode during a corresponding one of the display periods that follows the corresponding one of the sample periods the processing subsystem is configured to provide to the display device a corresponding display image that is based on a corresponding perceived image generated by the processing subsystem as a result of processing the received signals associated with nerve impulses transmitted by the at least one nerve in response to viewing the at least portion of the scene by the eye during the corresponding one of the sample periods.

Optionally, the display device includes at least one of a surface mounted display, head-mounted display, a head-up display, or holographic display.

Optionally, the system further comprises an interfacing arrangement for placing the processing subsystem in communication with the at least one nerve.

Optionally, the interfacing arrangement is external to the subject.

Optionally, the image is the perceived image.

Optionally, the image is a modified version of the perceived image.

Optionally, the image is the perceived image augmented to include an image of an object overlaid on the perceived image.

Optionally, the processing subsystem is further configured to: identify a data record associated with one or more elements of image data of the image, the one or more elements of the image data being associated with a spatial location of a portion of the image that contains at least part of the object, and initiate at least one responsive action in response to the identifying, the at least one responsive action being associated with the object in the image.

Optionally, the subject has a pair of eyes, and the display device is deployed to project images for viewing by both of the eyes of the subject.

Optionally, the eye of the subject is a first eye of the subject and the display device is deployed to project images for viewing by the first eye, and the system further comprises a second display device that is deployed to project images for viewing by a second eye of the subject, the second display device operable in a display mode and a non-display mode.

Optionally, the display device is configured to: operate in display mode when the second display device operates in non-display mode, and operate in non-display when the second display device operates in display mode.

There is also provided according to an embodiment of the teachings of the present invention a system for use with a subject having a brain that includes a region responsible for visual perception. The system comprises: a display device configured for deployment in spatial relation to the subject; and a processing subsystem for communicating with at least one nerve associated with an eye of the subject, the processing subsystem configured to: receive signals associated with nerve impulses transmitted by the at least one nerve in response to viewing a scene by the eye, process the received signals to generate a perceived image representative of a visual perception, by the region of the brain, of the scene, generate a display image by combining the perceived image with an image of an object such that the object appears as overlaid on the scene in the display image, provide the display image to the display device for viewing by the subject, and identify a data record associated with one or more elements of image data of the display image, the one or more elements of the image data being associated with a spatial location of a portion of the display image that contains at least part of the object.

Optionally, the processing subsystem is further configured to initiate at least one responsive action associated with the object in response to identifying the data record.

Optionally, the at least one responsive action includes at least one of activating or controlling at least one electronic device associated with the object.

Optionally, the at least one responsive action is selected from a plurality of responsive actions, each responsive action of the plurality of responsive actions being associated with a corresponding data record of a plurality of data records, each data record of the plurality of data records being associated with a corresponding one or more elements of the image data.

Optionally, the processing subsystem is configured to identify the data record in response to detecting an event associated with the portion of the display image that contains at least part of the object.

Optionally, the processing subsystem is further configured to initiate feedback that is provided to the subject in response to detection of an event associated with the portion of the display image that contains at least part of the object.

Optionally, the system further comprises: a haptic interface associated with the subject, and the processing subsystem is further configured to actuate the haptic interface to provide haptic feedback to the subject in response to detection of an event associated with the portion of the display image that contains at least part of the object.

Optionally, the object is one of a plurality of objects, the system further comprising: at least one storage medium for maintaining a plurality of data records that includes the data record, the plurality of data records being comprised of a plurality of subsets of data records, each subset being associated with a corresponding object of the plurality of objects.

There is also provided according to an embodiment of the teachings of the present invention a method for use with a subject having a brain that includes a region responsible for visual perception. The method comprises: deploying a processing subsystem in communication with: i) at least one nerve associated with an eye of the subject, and ii) a display device deployed in spatial relation to the subject and configured to operate in a display mode and a non-display mode;

receiving, by the processing subsystem, signals associated with nerve impulses transmitted by the at least one nerve in response to viewing at least a portion of a scene by the eye during a sample period, the sample period coinciding with operation of the display device in the non-display mode; processing, by the processing subsystem, the received signals to generate a perceived image representative of a visual perception of the scene by the region of the brain; and providing to the display device, by the processing subsystem, an image for display during a display period that coincides with operation of the display device in the display mode, the image being based on the perceived image.

There is also provided according to an embodiment of the teachings of the present invention a method for use with a subject having a brain that includes a region responsible for visual perception. The method comprises: deploying a processing subsystem in communication with: i) at least one nerve associated with an eye of the subject, and ii) a display device deployed in spatial relation to the subject and configured to operate in a display mode and a non-display mode; receiving, by the processing subsystem, signals associated with nerve impulses transmitted by the at least one nerve in response to viewing a scene by the eye; processing, by the processing subsystem, the received signals to generate a perceived image representative of a visual perception, by the region of the brain, of the scene; generating, by the processing subsystem, a display image by combining the perceived image with an image of an object such that the object appears as overlaid on the scene in the display image; providing to the display device, by the processing subsystem, the display image for viewing by the subject; and identifying, by the processing subsystem, a data record associated with one or more elements of image data of the display image, the one or more elements of the image data being associated with a spatial location of a portion of the display image that contains at least part of the object.

Within the context of this document, the term "perceived image" generally refers to an image that is generated by converting nerve impulses or signals associated with nerve impulses to image data, whereby the nerve impulses that are converted (or the nerve impulses associated with the signals that are converted) are nerve impulses that are transmitted from the eye or eyes of a subject to the visual processing region of the brain of the subject, which is a region of the brain of the subject that is responsible for visual perception, in response to the subject viewing a scene. In other words, the "perceived image" is a generated or manufactured image that represents what the subject sees with his/her eye(s) when viewing the scene. The term "eye image" is also used interchangeably with the term "perceived image".

Also within the context of this document, the term "display image" generally refers to an image that is based on the "perceived image" and that is provided to a display device for display. In other words, the "display image" has image elements or components that are elements/components of the "perceived image" or that are derived from elements/components of the "perceived image". In certain cases, the "display image" can be the "perceived image" itself. In other cases, the "display image" is a modified version of the "perceived image". This modified version of the "perceived image" can be, for example, the "perceived image" which has been modified to change one or more image parameters and/or features for one or more elements (e.g., pixels) of the "perceived image", including, but not limited to, color, brightness, contrast, size and the like. The modified version of the "perceived image" can also be a cropped version of the "perceived image", whereby some of the elements of the "perceived image" are removed (i.e., deleted). The modified version of the "perceived image" may also be the "perceived image", or a modified version thereof according to one or more of the modifications described above, augmented to include elements or components of other images, such as elements or components corresponding to images of one or more objects that are not a part of the scene upon which the "perceived image" is based.

Also within the context of this document, the term "image data" generally refers the data items or data objects associated with a given image that maintain the image information for that image data. The image data can include, for example, pixel data and/or information for each pixel of the image, including, for example, color values, intensity values, and the like.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIG. 3 is a schematic representation of an example deployment of the processing subsystem of FIGS. 1 and 2 in which the processing device interfaces with the visual processing region of the brain of the subject via implantation at the optic nerves, according to an embodiment of the present invention;

FIG. 4 is a schematic representation of an exemplary wired interface that includes an electrode array that can be used for interfacing between the processing subsystem and the visual processing region of the brain of the subject, according to an embodiment of the present invention;

FIG. 5 is a schematic representation of an exemplary wireless interface that can be used for interfacing between the processing subsystem and the visual processing region of the brain of the subject, showing a transmitter unit connected to the processing device, and an electrode array connected to a receiver unit, according to an embodiment of the present invention;

FIG. 6 is a schematic representation of a display image projected by the display device as seen from the point of view of the subject when looking at the display device, in which the display image is a perceived image of a real scene viewed by the subject augmented to include a virtual object;

DESCRIPTION OF THE PREFERRED EMBODIMENTS

Figure 2:
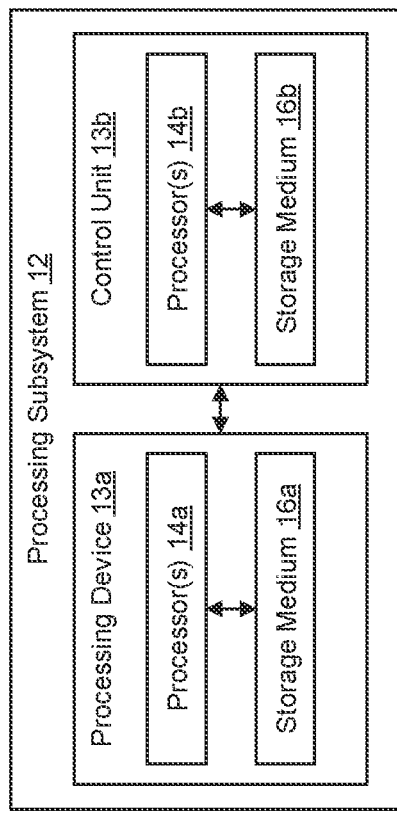
FIG. 2 is a block diagram of the processing subsystem of FIG. 1, showing the processing subsystem as exemplarily including a processing device and a control unit, according to an embodiment of the present invention.

Embodiments of the present invention provide systems and methods for displaying images to subjects.

The principles and operation of the systems and methods according to present invention may be better understood with reference to the drawings accompanying the description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Figure 1:
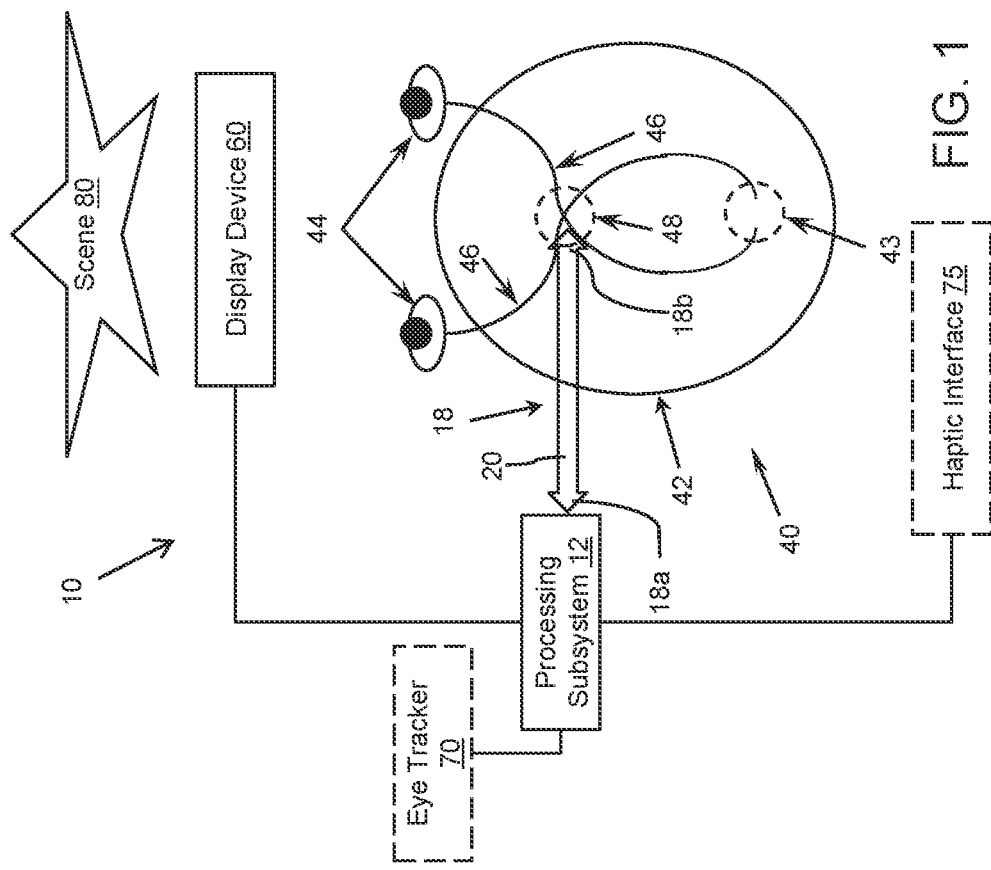
FIG. 1 is a schematic representation of a system having a processing subsystem for converting nerve impulses, transmitted to the visual processing region of the brain of a subject, into image data and for providing display images that are based on the image data to a display device, according to an embodiment of the present invention.

Referring now to the drawings, FIG. 1 is a schematic representation of a system, generally designated 10, according to an embodiment of the present invention. Generally speaking, the system 10 includes a computerized processing subsystem 12 (referred to hereinafter interchangeably as "processing subsystem") for interfacing (communicatively coupling) with a visual processing region 43 of the brain 42 of a subject (also referred to as a "user") 40 via, for example, at least one nerve 46 illustrated here as a pair of nerves 46. The visual processing region 43 is the region of the brain that is responsible for visual perception. In the illustrated example embodiment, the subject 40 is a human subject, and therefore the visual processing region 43 of the brain 42 is the visual cortex. In the illustrated embodiment, the processing subsystem 12 is coupled to at least one of the optic nerves 46, which is a paired cranial nerve that serves as a pathway between the eyes 44 and the brain 42 of the subject 40. It is noted, however, and as will become apparent from the subsequent sections of the present disclosure, embodiments of the present invention are also applicable to non-human animal subjects that have regions of the brain that perform visual processing and are responsible for visual perception.

The system 10 also includes a display device 60 that is communicatively coupled to the processing subsystem 12 and is configured to be deployed in spatial relation to the subject 40. In certain deployment configurations, the display device 60 is deployed in facing relation to eye(s) 44 such that the subject 40 can view the display device 60 with his/her eye(s) 44 without moving his/her body or head, whereas in other deployment configurations the display device 60 is deployed in non-facing relation to the eye(s) 44 (for example behind the subject 40) such that the subject 40 needs to move his/her head and/or body to view the display device 60. In the non-limiting deployment configuration illustrated in FIG. 1, the display device 60 is deployed between a scene (represented here schematically as a star 80) and at least one of the eyes 44 of the subject 40. It is noted, however, that other deployment configurations of the display device 60 are contemplated herein, including, for example, deployment configurations in which the display device 60 is adjacent to the scene 80 (for example to the side of, or behind, the subject 40) such that the subject 40 must shift his/her gaze direction and or head or body position to shift between viewing the scene 80 and the display device 60.

The display device 60 can be implemented in various ways, including, but not limited to, a head-up display (HUD), a head-mounted display (HMD), for example as goggles or in an eyeglass form factor, a holographic display, a surface (e.g., wall, table, desk, etc.) mounted electronic display such as, for example, a liquid crystal display (LCD) screen, a light-emitting diode (LED) display, a projection display, and the like. Note that projection displays typically include an image projection device, which can be an opto-mechanical device such as a movie projector, that projects images onto a suitable background that is capable of displaying such images. Such backgrounds can include, for example, projection screens which consist of a white and/or reflective surface supported by a support structure, but may also include wall structures and the like.

As will be discussed, the display device 60 is operative to display images that can be viewed by the subject 40, and in certain embodiments is configured to switch between operating in a display mode, in which the display device 60 projects (i.e., displays) image for viewing by the subject 40, and a non-display mode in which no images are projected by the display device 60. Operation of the display device 60 in display mode places the system 10 in a display mode, and operation of the display device 60 in non-display mode places the system 10 in a non-display mode.

The processing subsystem 12 is configured to perform processing and control functions. FIG. 2 shows a block diagram of the processing subsystem 12 according to certain non-limiting embodiments in which a functional subdivision between processing and control functions is provided by means of a computerized processing device 13a that performs processing related functions, and a computerized control unit 13b that performs control related functions. In the illustrated non-limiting embodiment, the processing device 13a and the control unit 13b include one or more processors 14a and one or more processors 14b, respectively. The processors 14a and 14b are respectively coupled to computerized storage mediums 16a and 16b. The computerized storage mediums 16a and 16b can be, for example, computerized memories or the like. The one or more processors 14a and 14b can each be implemented as any number of computerized processors, including, but not limited to, microprocessors, microcontrollers, application-specific integrated circuits (ASICs), field programmable gate arrays (FPGAs), digital signal processors (DSPs), field-programmable logic arrays (FPLAs), and the like. In microprocessor implementations, the microprocessors can be, for example, conventional processors, such as those used in servers, computers, and other computerized devices. For example, the microprocessors may include x86 Processors from AMD and Intel, Xeon® and Pentium® processors from Intel, as well as any combinations thereof. Implementation of the one or more processors 14a and 14b as quantum computer processors is also contemplated herein. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. It is noted that above-mentioned implementations of the one or more processors 14a and 14b represent a non-exhaustive list of example implementations. It should be apparent to those of ordinary skill in the art that other implementations of the processing device are contemplated herein, and that processing technologies not described herein or not yet fully developed, such as biological processors or organic semiconductors in the field of biological computing technologies, may be suitable for implementing any of the processing devices discussed herein.

Each of the storage mediums 16a and 16b can be any storage media, which although shown as a single component for representative purposes, may each be multiple components. The storage mediums 16a and 16b can be implemented in various ways, including, for example, one or more volatile or non-volatile memory, a flash memory, a read-only memory, a random-access memory, and the like, or any combination thereof. In certain embodiments, the storage medium 16a can include one or more components for storing and maintaining a mapping function or functions (which will be discussed further below), and at least one component configured to store machine executable instructions that can be executed by the one or more processors 14a.

Although FIG. 2 represents a functional subdivision in which the processing device 13a performs processing related functions and the control unit 13b performs control related functions, other subdivisions of processing and control also fall within the scope of the present invention. For example, in certain embodiments, the processors 14a of the processing device 13a can perform both processing and control functions thereby rendering moot the need for the control unit 13b, whereas in other embodiments the processors 14b of the control unit 13b can perform both processing and control functions thereby rendering moot the need for the processing device 13a. In yet another embodiment, each of the processors 14a and 14b may perform both processing and control functions, and the processing and/or control tasks for the processors 14a and 14b may dynamically change based on changing processing and control requirements.

The following paragraphs describe the processing related functions that are performed by the processing subsystem 12. Within the context of the non-limiting example embodiment illustrated in FIG. 1, these processing related functions are performed by the processing device 13a, however, as discussed above, other subdivisions of processing fall within the scope of the present invention.

Bearing the above in mind, the processing subsystem 12 is operative to receive signals associated with nerve impulses that carry image information and that are transmitted to the region 43 of the brain 42. The received signals can be the nerve impulses themselves, or can be signals which are produced (i.e., generated) in response to measurement or sampling of the nerve impulses by some microdevice, for example having microelectrodes or microtransducers, associated with the processing subsystem 12. This process of receiving signals by the processing subsystem 12 is generally referred to herein as "collecting nerve impulses". The nerve impulses are typically transmitted by the nerves 46, along the path from the eyes 44 to the region 43 of the brain 42, in response to viewing of a scene by the eyes 44 (referred to herein interchangeably as one or more visual stimuli (light) provided to the eyes 44). As discussed in the background, the light corresponding to the scene is sensed by photoreceptors in the eyes 44, and are converted into nerve impulses that are transmitted to the brain 42 by the optic nerves 46, to be interpreted by the brain 42 as sight and vision. This interpretation of nerve impulses by the brain 42 is referred to herein as "visual perception" or "perception".

The processing subsystem 12 is further operative to process the received signals (collected nerve impulses) so as to generate (produce) image data (a perceived image) that is representative of the perception (by the subject 40) of the scene. In other words, the generated image data (the perceived image) is representative of what the subject 40 sees with his/her eyes 44 when the eyes 44 view (i.e., are exposed to) the scene. The processing performed by the processing subsystem 12 converts the nerve impulses to image data by applying to the signals (collected nerve impulses) the above-mentioned mapping function or functions. The mapping function(s) includes mapping data, and maps between nerve impulses and image data, i.e., provides a transformation from nerve impulses to image data and vice versa, such that the received signals (that are representative of nerve impulses) are converted (transformed) to image data as a result of the application of the mapping function by the processing subsystem 12. This nerve impulse to image data mapping function is preferably a one-to-one mapping, and is referred to hereinafter interchangeably as an "impulse-image mapping". By a one-to-one mapping, it is meant that a single nerve impulse signal maps to a single image data signal, and vice versa. Various example methods for generating an impulse-image mapping are described in commonly owned U.S. Pat. No. 11,395,620, which is incorporated by reference in its entirety herein. The aforementioned patent also provides examples for storing and maintaining the impulse-image mapping, as well as examples for applying the impulse-image mapping to convert nerve impulses to image data. These examples, for generating, storing, maintaining, and applying the impulse-image mapping are also applicable to embodiments of the present disclosure.

In certain embodiments, the processing subsystem 12 is further operative to process received image data, that is representative of an image of a scene or object, to convert the image data into a sequence of nerve impulses, and to provide the nerve impulses to the region 43 such that the subject 40 visually perceives the scene or object as if the subject 40 had viewed the scene with his/her eyes 44. The processing subsystem 12 processes the received image data by applying to the image data the impulse-image mapping (since the impulse-image mapping is a two-way mapping, i.e., converts from nerve impulse to image data and vice versa). In certain embodiments, the processing subsystem 12 provides the nerve impulses to the region 43 via the nerves 46 by inducing nerve transmission of the nerve impulses. In certain embodiments, the processing subsystem 12 converts the image data to signals (e.g., electrical signals) that correspond to nerve impulses, and provides the nerve impulses to the nerves 46 by sending the converted signals to a microdevice, for example one or more microelectrodes or microtransducers, implanted in the subject 40 (e.g., at or on a portion of the nerves 46 or brain 42) that induces transmission of nerve impulses corresponding to the converted signals.

As will be discussed in further detail below, the image data that is to be received and processed by the processing subsystem 12 for conversion to nerve impulses can be image data captured by an imaging device (e.g., camera) electrically associated with the processing subsystem 12, or can be image data retrieved from a computerized storage (i.e., memory) linked to, connected to, or otherwise associated with, the processing subsystem 12.

The aforementioned U.S. Pat. No. 11,395,620 also provides examples for applying the impulse-image mapping to image data to convert the image data to nerve impulses. These examples are also applicable to embodiments of the present disclosure.

With continued reference to FIG. 1, the communicative coupling of the processing subsystem 12 to the region 43 can be effectuated by a machine-subject interfacing arrangement 18 (referred to hereinafter interchangeably as "interface") that places the processing subsystem 12 (and in this example, processing device 13*a*) in communication with the region 43 of the brain 42. In certain embodiments, the interface 18 can include two interfacing portions, namely a first interfacing portion 18*a* and a second interfacing portion 18*b*. The first interfacing portion 18*a*, also referred to as electronics interfacing portion 18*a*, is connected to the processing device 13*a*. The second interfacing portion 18*b*, also referred to as a subject interfacing portion 18*b*, can be connected or coupled to the region 43 of the brain 42. The two portions 18*a*, 18*b* are interconnected via a linking portion 20 which in certain embodiments can provide a wired connection between the two portions 18*a*, 18*b*, and in other embodiments can provide a wireless connection between the two portions 18*a*, 18*b*.

Various deployment configurations for achieving communicative coupling of the processing subsystem 12 to the region 43 are contemplated herein, and several of these deployment configurations will be described in further detail below. The deployment configurations described herein require some type of surgical implantation, which can employ invasive or semi-invasive techniques. For example, invasive techniques can include implantation by surgically accessing the subject's optic nerve and/or region through the subject's skull (i.e., surgically opening the skull). Surgeries performed on the brain, in particular the visual cortex and the optic nerve, have become common over the years, and it is asserted that a trained human surgeon and/or a robotic surgeon (such as used by the Neuralink Corporation of San Francisco, USA) can perform the necessary implantation. Semi-invasive techniques can include, for example, implantation by accessing the optic nerves or the optic chiasm through the nasal passageway via the sphenoid sinus. Before describing several deployment configurations, it is noted that the deployment configurations described herein are exemplary only and represent only a non-exhaustive subset of possible deployment options for the processing subsystem 12. Other deployment options may be possible, as will be apparent to those of skill in the art.

In one example deployment configuration according to certain non-limiting embodiments, the processing subsystem 12 communicates with the optic nerves 46 by tapping the optic nerves 46 via the interface 18. In such a deployment configuration, the subject interfacing portion 18*b* can be surgically implanted at or on a segment (section, portion) of the optic nerves 46, which in certain non-limiting implementations can be effectuated by first surgically cutting the optic nerves 46 to produce cut ends of the optic nerves 46, and then connecting the subject interfacing portion 18*b* to the cut ends. In such a deployment configuration, the processing subsystem 12 preferably remains external to the brain 42 of the subject 40. When the processing subsystem 12 is external to the subject 40, the subject interfacing portion 18*b* is surgically implanted at or on the optic nerves 46 together with either the entirety of the linking portion 20, or a segment of the linking portion 20 that connects to the subject interfacing portion 18*b*. If only the segment of the linking portion 20 that connects to the subject interfacing portion 18*b* is surgically implanted, the remaining segment of the linking portion 20, which connects to the electronics interfacing portion 18*a*, is external to the subject 40. Preferably, the segment of the optic nerves 46 at or on which the subject interfacing portion 18*b* is surgically implanted is the optic chiasm 48, which is the portion of the brain 42 at which the optic nerves 46 cross each other.

In another example deployment configuration, the processing subsystem 12 is deployed external to the subject, and the subject interfacing portion 18*b* is surgically implanted at or on the region 43 together with either the entirety of the linking portion 20 or a segment of the linking portion 20 that connects to the subject interfacing portion 18*b*. If only the segment of the linking portion 20 that connects to the subject interfacing portion 18*b* is surgically implanted, the remaining segment of the linking portion 20, which connects to the electronics interfacing portion 18*a*, is external to the subject 40. Such an example deployment configuration is schematically illustrated in FIG. 1.

In yet another example deployment configuration according to certain non-limiting embodiments, the processing device 13*a* itself, together with the entirety of the interface 18, can be implanted at or on the region 43. In another example deployment configuration according to non-limiting embodiments, the processing device 13*a* is implanted at or on a segment of the optic nerves 46. FIG. 3 schematically illustrates such deployment configuration. Here, the implantation can be effectuated, for example, by first cutting the optic nerves 46 to produce cut ends 50*a*, 50*b* of the optic nerves 46, and then deploying the processing device 13*a* at the sight of the cut and connecting the cut ends 50*a*, 50*b* of the optic nerves 46 to the processing device 13*a* via interface 18. In such a deployment configuration, the segment of the optic nerves 46 at or on which the processing device 13*a* is implanted is preferably, but not necessarily, the optic chiasm 48, whereby the optic nerves 46 are surgically cut (to produce cut ends 50*a*, 50*b*) at the optic chiasm 48. It is noted that in embodiments in which the processing device 13*a* or the interface 18 is surgically implanted at the optic nerve 46, care should be taken to ensure that the cut ends 50*a*, 50*b*, to which the processing device 13*a* is interfaced, correspond to the same nerve.

Non-invasive deployment configurations are also contemplated herein. For example, the interface 18 can be provided by way of an optical magnetic field sensor arrangement or a non-contact modulation arrangement employing, for example, optic, magnetic, or ultrasound techniques. In such configurations, the interface 18 (and its related components) as well the processing device 13*a* (and all subcomponents of the processing subsystem 12) are completely external to the brain 42. The external interface 18 picks up brain signals at the region 43 via non-contact or non-invasive contact means, and provides those picked up brain signals to the processing device 13a.

It is noted herein that the processing subsystem 12 can employ various techniques for obtaining nerve impulses (and their representative electrical signals) from the nerves 46 of the subject and for providing nerve impulses (converted from image data) to the nerves 46 to induce transmission (by the nerves 46) of the provided nerve impulses. Such techniques may typically rely on employing microdevices, such as microelectrodes or microtransducers, for measuring (receiving) nerve impulses and producing electrical signals in response thereto, and/or for stimulating the nerves 46 with electrical signals so as to induce transmission of the corresponding nerve impulses. Various entities have conducted research, development, and experimentation on connection and interfacing of computer processing devices to the brain, tissue, and nerves via implantation or other invasive or semi-invasive means. One example of such research can be found in a publication by the University of Luxembourg in 2019 entitled "CONNECT—Developing nervous system-on-a-chip" (available at https://wwwfr.uni.lu/lcsb/research/developmental_and_cellular_biology/news/connect_developing_nervous_system_on_a_chip), which describes culturing individual nervous system components and connecting the components in a microfluid chip (integrated circuit).

Examples of research and experimentation in the field of brain-machine interfacing is described in an article published in Procedia Computer Science in 2011, entitled "Brain-Chip Interfaces: The Present and The Future" by Stefano Vassanelli at the NeuroChip Laboratory of the University of Padova in Italy. In one example, computerized processing devices are interfaced to neurons with metal microelectrodes or oxide-insulated electrical microtransducers (e.g., electrolyte-oxide-semiconductor field-effect transistors (EOSFETs) or Electrolyte-Oxide-Semiconductor-Capacitors (EOSCs)) to record (i.e., measure) or stimulate neuron electrical activity. In another example, large-scale high-resolution recordings (i.e., measurements) from individual neurons are obtained using a processing device that either employs or is coupled to a microchip featuring a large Multi-Transistor-Array (MTA). In yet a further example, a microchip featuring a large MTA is used to interface with the cells in vitro by deploying the MTA in contact with brain tissue, where the signals corresponding to nerve impulses are, in one example, in the form of local-field-potentials (LFPs).

An example of a brain-machine interface device is the Neuralink device, developed by Neuralink Corporation of San Francisco, USA. The Neuralink device includes an ASIC that digitizes information obtained from neurons via microelectrodes.

Bearing the above in mind, the following paragraphs provide a high-level description of an interface 18 that can be used for connecting/interfacing the processing subsystem 12 to the subject 40 so as to provide a machine-brain interface, according to non-limiting example embodiments of the present invention.

With continued reference to FIGS. 1-3, refer also to FIG. 4, which illustrates a schematic representation of the interface 18 according to a non-limiting embodiment of the invention. Here, the subject interfacing portion 18b includes an electrode array 22, having a plurality of electrodes 23, that is deployed at or on the optic nerves 46 (e.g., at or on the optic chiasm 48). The electrodes 23 are preferably microelectrodes, such as EOSFETs or EOSCs. In embodiments in which the processing subsystem 12 is operative to convert nerve impulses to image data, the electrode array 22 is operative to measure nerve impulses transmitted by the optic nerves 46 and produce (in response to the measurements) electrical signals associated with (and representative of) the nerve impulses, and provide those signals to the processing subsystem 12 (in the illustrated example the signals are provided to the processing device 13a) in order to enable the processing device to collect the nerve impulses and process the electrical signals that correspond to (i.e., represent) the nerve impulses. In the illustrated embodiment, the linking portion 20 can be implemented as a wire or cable that provides a physical transmission medium along which the electrical signal can propagate to the processing device 13a. In certain embodiments, the interface 18 can employ a transducer (preferably a microtransducer as discussed above) as part of the subject interfacing portion 18b, either instead of or in addition to electrode array 22. The transducer can be used together with the processing device 13a for conversion of nerve impulses to digital image data. For example, the transducer can generate electrical signals in response to receiving (measuring) nerve impulses transmitted by the optic nerves 46. The generated electrical signals correspond to (i.e., are representative of) the nerve impulses, and are provided to the processing device 13a for processing using the impulse-image mapping.

In embodiments in which the processing subsystem 12 is operative to convert the image data to nerve impulses and transmit the nerve impulses to the brain 42 via the optic nerves 46 such that the nerve impulses are interpreted by the brain 42 as sight/vision, the transmission of the nerve impulses can be effectuated by stimulation of one or more neurons of the optic nerves 46 by a microdevice, e.g., the electrode array 22 (or a transducer). Generally speaking, in such embodiments the processing subsystem 12 can convert (using the impulse-image mapping) image data to nerve impulses (or electrical signals that represent nerve impulses) that are to be transmitted by the nerves 46. The processing subsystem 12 then provides the nerve impulses to the nerves 46 to induce nerve transmission of the nerve impulses (or provides the electrical impulses to the nerves 46 to induce nerve transmission of the nerve impulses represented by the electrical impulses). In certain embodiments, the inducing of nerve transmission can be effectuated by the processing subsystem 12 providing electrical signals to the electrode array 22 (or a transducer), which stimulates the neurons of the optic nerves 46 in accordance with the electrical signals so as to induce transmission of corresponding nerve impulses.

FIG. 5 illustrates another embodiment that employs wireless signal transmission for providing electrical signals to the microdevice, represented here as electrode array 22. Here, the processing subsystem 12 is connected to a transmitter (Tx) unit 24 via a wire or cable 25, and the electrode array 22 is connected to a receiver (Rx) unit 26 via a wire or cable 27. In the illustrated example, the connection of the wire or cable 25 is made to the processing device 13a. The Tx unit 24 includes transmitter circuitry and components for transmitting the electrical signals produced by the processing subsystem 12 via a wireless interface to the Rx unit 26. The Rx unit 26 includes receiver circuitry and components which receive the electrical signals, and provide the received signals to the electrode array 22 which stimulate the nerves 46 to induce the nerves 46 to transmit nerve impulses corresponding to the electrical signals.

In certain embodiments, the wireless transmission can be RF signal transmission. In such embodiments, the transmitter circuitry and components of the Tx unit 24 can include, for example, signal transmission electronics and components such as one or more antenna, digital-to-analog conversion circuitry, signal modulators, filters, amplifiers, etc., and the receiver circuitry and components of the Rx unit 26 can include, for example, signal reception electronics and components such as one or more antennas, filters, amplifiers, demodulators, etc. In other embodiments, the wireless transmission can be indictive signal transmission whereby the Tx unit 24 and the Rx unit 26 are operative to transmit and receive, respectively, using inductive signal transmission means. In such embodiments, for example, the Tx unit 24 can include inductive coils, and the Rx unit 26 can include an induction receiver.

As mentioned above, in certain embodiments the interface 18 can provide non-contact or non-invasive contact between the processing subsystem 12 and the region 43. For example, the interface 18 can include, for example, an optical magnetic field sensor arrangement or a non-contact modulation arrangement employing, for example, optic, magnetic, magnetic resonance imaging (MRI), or ultrasound techniques.

In certain embodiments, in particular embodiments in which the processing device 13*a* is implemented as a biological processor or biological processing element that is cultured or grown in the subject, the interface 18 is the processing device 13*a* itself.

It is noted that in certain embodiments, the interfacing arrangement 18 can include multiple interfaces. For example, a first interface can be used to effectuate conversion of image data to nerve impulses. The first interface can employ an electrode array 22 or microtransducers (implemented, for example, as EOSCs) connected or linked to the processing subsystem 12 (e.g., the processing device 13*a*) via a wired connection (for example as shown in FIG. 4) or wireless connection (for example as shown in FIG. 5). A second interface can be used to effectuate conversion of nerve impulses to image data. The second interface can employ an electrode array 22 and/or microtransducers (implemented, for example, as EOSFETs) connected or linked to the processing subsystem 12 (e.g., the processing device 13*a*) via a wired connection (for example as shown in FIG. 4). In other embodiments, the second interface can employ non-contact or non-invasive contact means (e.g., an optical magnetic field sensor arrangement or a non-contact modulation arrangement).

As discussed above, in certain embodiments the processing subsystem 12 is also operative to convert image data representing a scene or an object into a sequence of nerve impulses, and then provide the nerve impulses to the region 43 such that the subject 40 visually perceives the scene or object as if the subject 40 had viewed the scene with his/her eyes 44. However, implementation of such embodiments may be technically challenging and invasive as they may require some form of implantation in the subject 40, for example implantation of the processing device 13*a* and/or implantation of a microdevice that receives the nerve impulses or representative electrical signals from the processing subsystem 12 and induces transmission of the nerve impulses by nerves 46 associated with the microdevice. Therefore, it is a particular feature of certain embodiments of the present disclosure to provide non-invasive alternative solutions for displaying images to the subject by employing a display device 60 that is operative to selectively (and controllably) display images to the subject that are based on images generated from the subject's vision of a scene. According to such embodiments, the processing subsystem 12 (for example the processing device 13*a*) is operative to receive signals associated with nerve impulses transmitted by the nerve(s) 46 in response to the eye(s) 44 viewing the scene 80 during a sample period that coincides with the display device 60 operating in the non-display mode. The processing subsystem 12 processes the received signals by applying the impulse-image mapping, thereby generating a perceived image (i.e., converting the nerve impulses to image data of the perceived image) whereby the perceived image is representative of a visual perception of the scene 80 by the region 43 of the brain 42. The processing subsystem 12 is further operative to provide to the display device 60 an image for display (referred to herein as a "display image"), that is based on the generated perceived image, during a display period that coincides with the display device 60 operating in the display mode. Thus, during the display period, the subject 40 is able to view the display image as displayed by the display device 60. As will be discussed, the display image can include elements of the perceived image.

In one example, the display image is the perceived image, i.e., the display image is an unmodified version of the perceived image. This may be useful in various situations, for example calibrating and/or testing the system 10.

In another example, the display image is a modified version of the perceived image. For example, as discussed in previous sections of the present document, the display image can be the perceived image which has been modified to change one or more image parameters or features of one or more image elements (e.g., pixels), including, for example, one or more of color, brightness, contrast, and size, and/or modified to crop the perceived image (for example by removing pixel data). The display image can also be the perceived image (either the raw perceived image, or a modified version of the perceived image as described above) which has been augmented to include an image of the object such that the object appears as overlaid on the scene in the display image.

The modification of the perceived image can be performed by the processing subsystem 12, for example by adding and/or removing and/or changing elements (e.g., pixel information) in the image data of the perceived image. Further details of how the processing subsystem 12 can modify the perceived image, and ways in which the perceived image can be modified by the processing subsystem 12, are provided in the aforementioned U.S. Pat. No. 11,395, 620.

Within the context of the present disclosure, when the subject 40 views a display image that is a perceived image which has been modified in some way, for example by the processing subsystem 12, to include an image representative of an object, the object as viewed within the display image is referred to as a "virtual object". The term "virtual object" is used here because the object is virtual in the sense that the object is not part of the scene that the subject has viewed during the preceding sample period (and is therefore not a part of the scene upon which the perceived image is based), and is therefore, from the subject's perspective, a "virtual" part of the display image. This virtual object may be based on any real-world object, including, for example, a computer input device such as a computer keyboard, computer mouse and the like, an interactive display screen, a head-up display such as a head-up display (HUD) in a motor vehicle or in a cockpit of an aircraft, an electronic appliance such as a smartphone, tablet, digital radio receiver, speaker system, a household appliance such as an oven, microwave oven, dishwasher, or laundry appliance (e.g., washing machine, dryer), and the like. For example, image data that is descriptive/representative of one of such aforementioned real-world objects can be combined, for example by the processing subsystem 12, with the perceived image to produce the display image. As will be discussed, such image data can come from various sources, including, but not limited to, memory devices and imaging devices. For example, such image data may be stored in a device, for example a memory, that is associated with the processing subsystem 12, As another example, a device, for example an imaging device (e.g., camera), associated with the processing subsystem 12, may capture an image or images of a real-world object so as to generate such image data.

FIG. 6 illustrates an example of a display image 90 that is projected by the display device 60 during the display period, as seen from the point of view of the subject 40 when looking at the display device 60. Here, the display image 90 is the perceived image (which is the image of the scene 80) augmented to include a virtual object (represented here schematically as a shaded four-pointed star 92). As a result, the subject 40, when viewing the display image 90, sees the virtual object 92 as being overlaid on the scene 80.

Parenthetically, also shown in FIG. 6 is a portion (represented schematically as a free-form shape 94) that provides a boundary region that encloses some or all of the object 92. The details of the portion 94 will be discussed in further detail below within the context of another aspect of the present disclosure which supports interaction with virtual objects and/or control of real-world objects associated with virtual objects. Such aspects are particularly useful in augmented reality types of applications.

In certain embodiments, the processing subsystem 12 is operative to controllably and repeatedly switch the display device 60 between a display mode, in which the display device 60 projects (i.e., displays) a display image, and a non-display mode in which the display device 60 does not display any images, such that the display device 60 alternatingly projects display images and no images to the subject 40. In other words, by switching the display device 60 between display and non-display modes, the processing subsystem 12 effectively switches the display device 60 between on and off states, whereby in the on state (display mode) the display device 60 projects a display image or images, and in the off state (non-display mode) the display device 60 does not project any images thereby allowing the subject to view the real-world scene.

It is noted that within the context of the non-limiting example embodiment illustrated in FIG. 1, controlled switching of the display device 60 is performed by the control unit 13b. In addition, the control unit preferably also manages the timing associated with switching between the display and non-display modes, as well as the parameters associated with the various periods, for example the duration of the sample period and the duration of the display period. It is noted, however, other subdivisions of control and timing function fall within the scope of the present invention, as discussed above.

In certain embodiments, for example when the display device 60 is implemented as a surface mounted display screen or when the display device 60 is implemented in an eyeglasses form factor occupying a small portion of an eyeglass lens, the display device 60 may permanently obscure a small portion of the subject's field of view (FOV) of the scene 80 when the display device 60 is deployed between the scene 80 and the eye(s) 44. In such embodiments, the display device 60 obscures (i.e., blocks) the small portion of the FOV regardless of the operating state of the display device 60. Preferably, the obscured portion is small enough that the eye(s) 44 of the subject 40 can still faithfully form an image of the scene 80. It is noted that obscuring the scene when the display device 60 operates in display mode can be critical to prevent the subject 40 from simultaneously viewing the real scene and the display image, thereby avoiding visual confusion on the part of the subject 40.

Parenthetically, it is noted that in embodiments in which the display device 60 is implemented as a projection display, the background, upon which the image projection device projects the images, can be deployed in any suitable spatial location relative to the subject so long as the image projection device can project images onto the background. For example, in one deployment configuration, the background can be deployed adjacent to the scene (for example to the side of, or behind, the subject) such that the subject must shift his/her gaze direction and or head or body position to shift between viewing the scene and the background. In another deployment configuration, the background may be deployed in facing relation to the subject's eye(s). In such a configuration, the background may also be interposed between the scene and the subject's eye(s), whereby the background partially obscures a preferably small portion of the subject's FOV of the scene. According to certain embodiments, when the background is deployed so as to be interposed between the scene and the subject's eye(s), the background itself can be incorporated as part of the scene and thus also a be part of the perceived image. In such embodiments, the processing subsystem 12 may modify the perceived image to remove or adjust the opacity level of the elements of the perceived image that correspond to the background.

In other non-limiting embodiments, the display device 60 is an at least partially transparent display, such that when the display device 60 operates in the non-display mode some or all (i.e., at least a portion) of the scene 80 is at least partially viewable to the eye(s) 44 through the display device 60. Various types of partially transparent displays (i.e., "see through displays") are known in the art. Such displays employ various display technologies, including, for example, holographic displays, LCD panels that are made transparent by employing twisted nematic liquid crystals with cross polarizers, and LED displays that utilize layers of glass on both sides of addressable LEDs. In certain embodiments, the display device 60 can be implemented as a HUD or HMD, for example as goggles or in an eyeglass form factor. Such HUD and HMD implementations can advantageously employ optical waveguides or substrates which make the HUD and HMD implementations partially transparent (see through) or non-transparent (non-see-through). Various optical waveguide technologies that provide see through and non-see-through displays are known in the art, including, for example, HoloLens from Microsoft of Redmond Washington, and the lightguide optical elements (LOEs) from Lumus Ltd. of Israel.

In certain embodiments, the display device 60 may only obscure the scene 80 when the display device 60 operates in display mode. The obscuring of the scene 80 by the display device 60 can be effectuated in various ways. In one non-limiting example, the obscuring of the scene 80 by the display device 60 can be effectuated by employing mechanical movement of the display device 60, for example deployment of a mechanical arm or mount, that is in mechanical driving relationship with the display device 60, that moves the display device 60 in and out of the light path between the scene and the eye(s) in synchrony with operation of the display device in display mode and non-display mode. In another non-limiting example, the obscuring of the scene 80 by the display device 60 can be effectuated by deploying a moving shutter or baffle that moves in and out of the light path between the display device and the scene in synchrony with operation of the display device in display mode and non-display mode. In yet another non-limiting example, a switchable polarization filter can be deployed between the display device and the scene. The polarization filter can be actuated to assume a first state, when the display device 60 operates in display mode, which blocks incident light from the scene, and actuated to assume a second state, when the display device 60 operates in non-display mode, which allows incident light from the scene to pass through the display device and reach the eye(s) 44. In all of the aforementioned examples, control of mechanical movement and/or state switching can be providing by the processing subsystem 12.

Figure 7:
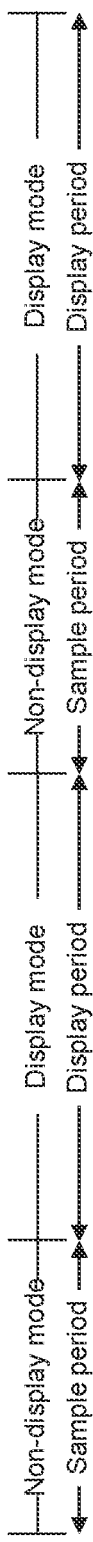
FIG. 7 is a timing diagram illustrating an alternating sequence of sample periods and display periods corresponding to operation of the display device in a non-display mode and a display mode, according to an embodiment of the present invention.
Figure 8:
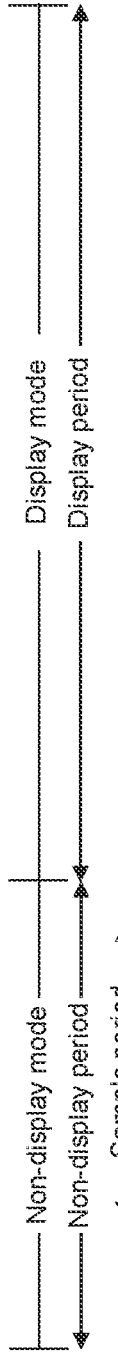
FIG. 8 is a timing diagram that is similar to FIG. 7, but showing a single timing cycle of operation of the display device in non-display mode and display mode, and in which the sample period for the non-display mode is a sub-period of a non-display period corresponding to operation of the display device in the non-display mode.

In certain embodiments, the sample period and the display period are non-overlapping periods, and can be adjacent periods such that when the display period ends the sample period begins and vice versa, for example as shown in the timing diagram illustrated in FIG. 7. Alternatively, there may be a small delay between the end of one period (e.g., sample period) and the start of the next period (e.g., display period). In certain embodiments, operation of the display device 60 in the non-display mode coincides with a non-display period which includes at least one sample period as a sub-period (or sub-interval) of the non-display period. FIG. 8 illustrates a timing diagram of one cycle of operation of the display device 60 in non-display mode and display mode for such an embodiment. Here, when the processing subsystem 12 switches the display device 60 to the non-display mode, the eye/eyes 44 captures/capture light from the scene such that nerve impulses carrying scene image information are transmitted to the region 43 of the brain 42 over the duration of the non-display period. The nerve impulses corresponding to the light captured by the eye(s) 44 during the sample period sub-interval of the non-display period are converted to image data by the processing subsystem 12 (by applying the impulse-image mapping). In other words, the processing subsystem 12 only converts a selected sampling of the nerve impulses that are transmitted during the non-display period.

Preferably, the sample period is a relatively short period as compared to the display period. For example, the display period may be one or more orders of magnitude greater than the sample period. For example, the sample period may be on the order of a few milliseconds, and the display period may be on the order of several seconds. The discrepancy in magnitude can be attributed to the fact that in human vision systems, when a series of images is captured by the eyes, the brain typically ignores individual images that do not conform to the series. For example, research has shown that an average human brain can process nerve impulses corresponding to scene snapshot images to form an entire scene image in as little as 13 milliseconds (https://news.mit.edu/2014/in-the-blink-of-an-eye-0116), and therefore one or more such snapshots that deviate from the series of snapshots can be discarded or ignored by the brain. As will be discussed, however, there may be situations in which the sample period and display period are of the same magnitude or approximately equal to each other. In addition, there may be situations in which the sample period is smaller than the display period.

Thus, according to embodiments of the present invention, the processing subsystem 12 (e.g., the control unit 13*b*) switches the display device 60 to the non-display mode to allow the eyes to view (i.e., capture images of) the scene 80 during a relatively short sample period, and then switches the display device 60 to display mode in order to project the display image that is generated based on the viewing of the scene in the preceding sample period. As discussed above, the display image is generated by the processing subsystem 12 by converting to image data (i.e., a perceived image) the nerve impulses that are transmitted by the nerve 46 to the region 43 in response to the eye(s) 44 viewing scene 80 during the sample period. This image data (i.e., the perceived image) can optionally be temporarily stored in memory (e.g., storage medium 16*a* and/or 16*b*, or any other data storage medium associated with the processing subsystem 12). The temporary storage allows the processing subsystem 12 to collect all of the image data necessary for building up the perceived image of the scene (thereby providing a type of buffering). The processing subsystem 12 can then operate on the image data (i.e., the perceived image) by modifying the image, for example changing pixel values in the image data by combining the perceived image with an image of an object. The image of the object can be retrieved from any suitable electronic device, including, for example a camera/imaging device associated with the processing subsystem 12, a memory associated with the processing subsystem 12 (e.g., storage medium 16*a* and/or 16*b*), and the like. In certain embodiments, the image of the object can be a brain generated image, such as an imagination image, that is stored in a memory associated with the processing subsystem 12. Examples of techniques for producing brain generated images, e.g., imagination images, are described in commonly owned U.S. patent application Ser. No. 17/863,480, filed on Jul. 13, 2022, whose disclosure is incorporated by reference in its entirety herein.

It is also noted that in certain preferred embodiments, the sample period coincides with non-blinking periods, such that the nerve impulses that are converted to image data to produce the perceived image exclude nerve impulses collected or transmitted during eye blinks. In certain embodiments, the sample period may be a non-continuous period which includes gaps or breaks which corresponding in time length to blink periods. In other embodiments, a guard interval can be imposed around the sample period (or periods) to ensure that no blink-related nerve impulses are converted by the processing subsystem 12. In one set of non-limiting embodiments, detection of blinks and associated blink periods is performed by a detection device, such as any suitable detection device as is known in the art. By way of non-limiting example, devices that can detect blinks and associated blink periods can include eye trackers which detect movement of the eye and its surrounding musculature, and eye blink sensors that utilize infrared sensors to determine when the eye is closed. In another set of non-limiting embodiments, the processing subsystem 12 performs blink detection by processing collected nerve impulses. The processing subsystem 12 may process the collected nerve impulses to detect blinks utilizing the fact that a nerve impulse that is generated and transmitted during a blink corresponds to a dark or blank image. Thus, for example, the processing subsystem 12 may convert one or more collected nerve impulses to image data and determine which of those collected nerve impulses correspond to nerve transmissions during a blink by analyzing the image data that is generated from the collected nerve impulses to identify image data representative of black or blank images. Once the processing subsystem 12 identifies the nerve impulses that generate image data representative of black or blank images, the processing subsystem 12 may flag or mark such collected nerve impulses, and refrain from using those flagged nerve impulses when generating the perceived image.

Once the processing subsystem 12 finishes combining the perceived image with the image of the object, the processing subsystem 12 provides the resultant display image to the display device 60 (i.e., the processing subsystem 12 transmits the image data of the display image to the display device 60), and controls the display device 60 to display (i.e., project) the display image during the display period (i.e., the processing subsystem 12 switches the display device 60 to display mode). In certain embodiments, for example in embodiments in which the display device 60 naturally occupies a large portion of the subject's FOV, it is preferable that the display device 60 obscures the subject's view of the scene when the display device 60 is switched to display mode, such that the subject cannot view the scene while viewing the display image on the display device 60.

The processing subsystem 12 may, in certain embodiments, repeatedly switch the display device 60 between display and non-display modes, whereby each time the display device 60 is switched to the non-display mode the subject 40 views the scene 80 during a corresponding sample period and the processing subsystem 12 generates a perceived image of the scene based on the nerve impulses collected during the sample period. When the processing subsystem 12 switches the display device 60 to display mode at the end of the sample period (i.e., when the next display period begins) the processing subsystem 12 provides to the display device the display image that is based on the perceived image generated during the preceding sample period. In this way, the scene portion of the display images is updated over time to account for incremental changes in the scene, as captured by the eye(s) 44 of the subject 40.

It is noted herein that conversion of nerve impulses to image data may be a power consuming and/or computational resource intensive task. It may therefore be advantageous to optimize (or nearly optimize) some of the control and timing parameters in order to reduce the power consumption and number of computational resources of the processing subsystem 12. The following paragraphs describe such control and timing optimization.

As alluded to above, the processing subsystem 12 can be configured to store image data that is converted from nerve impulses (in response to the eye(s) 44 viewing the scene during the sample period) in a memory associated with the processing subsystem 12 (e.g., storage medium 16a and/or 16b). According to certain embodiments, the processing subsystem 12 is configured to switch the display device 60 to the display mode once a sufficient amount of image data that corresponds to a "full" image of the scene has been converted from nerve impulses and stored in memory. The criteria for sufficiency of a "full" image can be parameterized, for example the processing subsystem 12 can check the image density against a threshold criterion to determine whether a "full" image has been generated. In certain embodiments, the processing subsystem 12 switches the display device 60 to display mode as soon as image data for a "full" perceived image of the scene has been generated from the nerve impulses. In certain embodiments, for example in embodiments in which the processing subsystem 12 is configured to modify the perceived image to include a virtual object, the processing subsystem 12 may delay or buffer transmission of the display image data (e.g., perceived image augmented to include the virtual object) to the display device 60 to account for the processing time required to generate the display image. For example, although the processing subsystem 12 may switch the display device 60 to display mode as soon as the processing subsystem 12 finishes generating image data for a "full" perceived image, the processing subsystem 12 may not immediately send the perceived image to the display device 60 and may instead continue processing the perceived image to augment the perceived image with a virtual object, and only then send the display image (in this case the augmented perceived image) to the display device 60 for projection to the subject.

The duration of the non-display period can be set by the processing subsystem 12, such that each time the processing subsystem 12 switches the display device 60 to the non-display mode, the scene becomes unobscured to the subject 40 by the display device 60 for the duration of the non-display period such that the brain can process nerve impulses that are transmitted in response to the eye(s) 44 collecting light from the scene during the non-display period. For example, if the non-display period is set to 150 milliseconds, and the brain 42 processes nerve impulses to form an entire/full scene image in 13 milliseconds, the brain will can approximately 11 scene images during the non-display period. The processing subsystem 12 may select for processing the nerve impulses corresponding to a single one of these formed scene images to convert the selected nerve impulses to image data. The selection of the nerve impulses for processing can be made by defining the duration of the sample period, for example by setting the sample period to be at least the amount of time it takes the brain to form an image. In certain preferred embodiments, the sample period can include a buffer or margin to account for processing delays and/or minor interruptions on the nerves 46. For example, the processing subsystem 12 can define the sample period to be approximately 15 milliseconds, which is based on the 13 milliseconds that it takes an average brain to form a full scene image plus a buffer of approximately 2 milliseconds.

In certain embodiments, the processing subsystem 12 can impose a time limit for completion of generating image data for a "full" perceived image. For example, if at the end of the allowed time limit the processing subsystem 12 has not converted enough of the received nerve impulses to form a full perceived image, the processing subsystem 12 may instead use a stored perceived image, for example from a prior (preferably immediately preceding) operating cycle of the display device 60 in non-display mode. The stored perceived image can be stored in any memory associated with the processing subsystem 12 (e.g., storage medium 16a and/or 16b) and can be retrieved from that memory by the processing subsystem 12. The processing subsystem 12 can then use the retrieved perceived image to produce the display image, for example by augmenting the retrieved perceived image to include the virtual object.

In certain embodiments, the processing subsystem 12 may set the duration of the display period such that the same perceived image (for example generated from nerve impulses collected during a prior or immediately preceding sample period) is used as basis for the display image that is projected by the display device 60 during the display period. The duration of the display period can be, for example, set according to an optimization strategy, to ensure that the basis perceived image is not a stale image, i.e., such that the perceived image is still representative, to some degree, of the current scene.

It is noted that the timing and control parameters of the system 10 can be case and/or user specific. For example, in a vehicular head-up display environment, such as in the cockpit of an aircraft or in the driver-side of a motor vehicle, the processing subsystem 12 preferably performs switching between operating modes of the display device 60 at a relatively high rate to account for rapid changes in the scene such that the subject can seamlessly perceive the changing real scene with a virtual object or objects overlaid thereon. In such a case, the display period is preferably the same as, or a slightly larger than (for example small integer multiple larger than), the sample period. For example, the sample period may constitute the entirety of the non-display period and be 15 milliseconds, and the display period may be 15 milliseconds or more, for example up to 60 milliseconds. In such an example, the virtual object or objects can include, for example, vehicle speed, vehicle altitude, vehicle fuel information (e.g., fuel gauge), navigation information (e.g., compass, traveling direction, etc.), and the like.

As another example, if the system is deployed in a situation in which the scene changes slowly over time, for example as part of an office workstation in which the display device 60 is implemented as a wall or table/desk mounted electronic display such as an LCD screen, the display period may be significantly larger than the sample period. For example, in such an office workstation deployment the sample period may be 15 milliseconds and part of a non-display period of 100 milliseconds, and the display period may be several hundreds of milliseconds or even several seconds or minutes (depending for example on the rate at which the scene changes). In such an example, the virtual object or objects can include, for example, objects related to or associated with the workstation or the person operating the workstation, including, for example, a clock, a list of tasks for the person operating the workstation (i.e., a "to do list"), reminders, notifications, computer files, and the like.

All of the aforementioned timing and control parameters can be adjusted, for example optimized, automatically by the processing subsystem 12 based on input from the subject 40, or can be adjusted manually by the subject 40. In certain embodiments, and as alluded to in previous sections of the present disclosure, it may be advantageous to configure the processing subsystem 12 to provide the perceived image to the display device 60 as the display image (i.e., without augmentation with virtual objects) to allow calibration and/or testing and/or optimization of the system 10, including calibration and/or optimization of the non-display period, sample period, and display period. In certain embodiments, if the current timing and/or control parameters fail to allow the processing subsystem 12 to collect all of the image data necessary for building up the perceived image of the scene, the processing subsystem 12 may provide the subject with an alert or a notification indicating the failure. In certain embodiments, in addition to providing such an alert or a notification, the processing subsystem 12 may keep the display device 60 in non-display mode or may actuate the display device 60 to display only virtual images until an input command is received from the subject 40. In other embodiments, the processing subsystem 12 may automatically adjust the timing and/or control parameters to ensure that a full perceived image is built-up.

In certain embodiments, the display device 60 is deployed so as to display images simultaneously to both eyes of the subject 40. However, other embodiments are contemplated herein in which the display device is duplicated such that there are a pair of display devices, where each display device projects images for a respective one of the eyes of the subject. For example, the system may include a first (left-eye) display device that projects images for viewing by only the left eye of the subject, and a second (right-eye) display device that projects images for viewing by only the right eye of the subject. Such embodiments are particularly suitable when the display device is implemented in a goggle or eyeglass form factor, where left-eye and right-eye display devices can be easily deployed in spatial relation to the corresponding left and right eyes of the subject. It is noted that in such a dual display device configuration, the processing subsystem 12 may independently operate the display devices to switch between display and non-display modes. Moreover, the display and non-display modes of the two display devices may identically coincide with each or may be altogether different and/or non-overlapping. For example, the first display device may be configured to operate in display mode when the second display device operates in non-display mode, and further configured to operate in non-display mode when the second display device operates in display mode. In other words, in this example, when one of the display device operates in display mode, the other of the display devices operates in non-display mode.

Parenthetically, it is noted that in general the display device duplication described above can be extended to any number of displays and corresponding number of eyes, in particular cases of more than two eyes. This may be particularly useful in situations in which the system is configured for deployment and use by an animal subject that has more than two eyes, for example certain invertebrate species. It is further noted that a display device for a given eye may include a set of displays that together operate as one display.

It is further noted that the processing subsystem 12 may additionally be configured to operate in a standby or bypass mode, for a given period of time, in which the processing subsystem 12 does not convert any collected nerve impulses to image data. Furthermore, the display device (or devices) may be further configured to operate in a conventional display mode, in which the display device projects any suitable type of image aside from the above-described display images, including images provided from an external device such as a memory or imaging device (e.g., camera). For example, the processing subsystem 12 may actuate the display device 60 to operate in the conventional display mode intermittently between switches between display and non-display mode. For example, the processing subsystem 12 may switch the display device to display mode so as to project a display image, and then may switch the display device to conventional display mode such that the display device projects an image that is not a display image, and then may switch the display device to non-display mode such that the display device does not project any images. As should be apparent, the aforementioned operation in conventional display mode is also applicable to dual display device configurations.

As mentioned, there may be several situations in which providing a display image, that is a modified version of the perceived image which is augmented to include a virtual object or objects, is useful. One particularly useful set of scenarios is where interaction with virtual objects (for example by the subject) and control (for example initiated by the subject or by an artificial intelligence (AI) platform) of real-world objects associated with virtual objects is desired. The following paragraphs describe embodiments which support interaction with virtual objects and control of real-world objects. In such embodiments, the processing subsystem 12 is operative to identify a data record (for example having metadata) that is associated with one or more elements of image data of the display image, which as discussed above is based on the perceived image and is thus also derived from nerve impulses that are transmitted in response to the eye(s) viewing a real-world scene. These one or more elements of the image data that are associated with the identified data record are also associated with a spatial location of a portion of the display image that contains at least part of the virtual object. The portion of the display image that contains at least part of the object provides a boundary region that encloses some or all of the object.

Referring again to FIG. 6, there is shown one non-limiting example, in which the portion (represented schematically as a free-from shape 94) completely surrounds the virtual object 92. It is noted, however, that in certain cases the portion 94 may not entirely surround the virtual object 92. For example, the portion 94 may surround only a part or parts of the virtual object 92, such that one or more parts of the virtual object 94 are outside of the boundary region.

The spatial location can be any location in space that is within or sufficiently close to (i.e., near) the portion 94, but it may be preferable that the spatial location be a location that is within the portion 94. In certain embodiments, the spatial location can be any location in two-dimensional space that is within or near the portion 94. Such a spatial location can thus be defined by a pair of spatial coordinates, for example x and y coordinates corresponding to the horizontal and vertical dimensions of the display image 90 respectively. In other embodiments, the spatial location can be any location in three-dimensional space that is within or near the portion 94. Such a spatial location can thus be defined by three spatial coordinates, for example x, y, and z coordinates corresponding to the horizontal, vertical, and depth dimensions, respectively, of the subject's 40 view of the display image 90.

The data record, optionally together with other similarly structured data records, forms a set of data records, which can be stored in a storage medium (e.g., memory or database) associated with the system 10, such as storage medium 16a and/or 16b. Each data record in the stored set of data records can store various attributes associated with the image data of the display image, and in particular attributes associated with the components of the image data pertaining to the virtual object. As will be discussed further below, each data record can also store other attributes such as virtual object spatial coordinates (in two- or three-dimensional space) as well as actions associated with the virtual object.

The processing subsystem 12 is operative to identify the data record, for example from the set of data records, that is associated with (i.e., corresponds to) the spatial location of the portion (e.g., portion 94) of the display image 90 that contains at least part of the virtual object 92. The processing subsystem 12 may identify the data record based in part on the image data of the display image, as well as metadata in the data record that is associated with the image data. This metadata may include, for example, the spatial location (coordinates) of virtual objects within display images, which can be stored as attributes in the data record.

The identification of the data record by the processing subsystem 12 can be in response to a detected event associated with the portion 94 of the display image 90 that contains at least part of the virtual object 92. In certain embodiments, the detected event can be detected by an algorithm executed by one of the processors of the processing subsystem 12, for example an AI algorithm. For example, the event that is detected can be a generic event, such as the mere presence of the virtual object in the display image, or the virtual object being located in a specific position within the display image. In certain embodiments, the detected event is a detected action that can be, without loss of generality, a subject-initiated action (i.e., the subject 40 initiates the action) on the portion 94 of the display image 90 that contains at least part of the virtual object 92.

Within the context of this document, the term "subject-initiated action" refers to any action whose genesis can be traced back to the subject. Examples of subject-initiated actions can include, but are not limited to, for example, gesturing (using the subject's hands or other part of the subject's body, or using a real object held or controlled by the subject, such as, for example, a stick pointer or laser pointer) towards the portion 94 of the display image 90 that contains at least part of the virtual object 92, pointing (using a part of the subject's body, or using a real object held or controlled by the subject, such as, for example, a stick pointer or laser pointer) at or on the portion 94 of the display image 90 that contains at least part of the virtual object 92, a voice activation command that is associated with a feature of the virtual object 92, and the like.

The detecting of the subject-initiated action can be performed by the processing subsystem 12 or by a component associated with the processing subsystem 12. By way of one non-limiting example, the processing subsystem 12 may detect such an action by processing collected nerve impulses that are transmitted in response to the subject viewing the action taking place. For example, if the action is initiated by the subject 40 pointing to the portion 94 with a pointing object (e.g., a part of the subject's body or a pointer device), the processing subsystem 12 may receive signals (collected nerve impulses) that are transmitted in response to the subject 40 seeing (with his/her eye(s) 44) the portion 94 being pointed to or at by the pointing object. The processing subsystem 12 may then process those received signals (by applying the impulse-image mapping) to convert the signals to a new image (i.e., generate new image data). The processing subsystem 12 may then compare elements of image data of the new image with the elements of image data of the display image 90 that correspond to the virtual object to determine whether the pointing action is at a spatial location that contains at least part of the virtual object 92. For example, the processing subsystem 12 can compare each pixel of the image data of the new image with each pixel of the image data of the display image 90 to determine if the two pixels (one from the new image and one from the display image 90) have the same or similar coordinates. For example, if the processing subsystem 12 identifies one or more pixels of the new image have the same or similar coordinates as one or more of the pixels of the display image 90 that correspond to the virtual object, the processing subsystem 12 can make a determination that there is a spatial overlap between the identified pixels of the new image and the virtual object pixels of the display image 90, and can then also make a determination that a subject-initiated action was performed.

In another example, the detecting of the subject-initiated action can be performed in cooperation with an eye tracking subsystem (i.e., an "eye tracker"). The eye tracker can be implemented as one or more cameras or any other sensor device that can detect and track eye gaze and eye movement and/or certain eye-related features such as blinks, all as is well-known in the art. An example embodiment that utilizes an eye tracker is illustrated in FIG. 1. Here, eye tracker 70 can optionally be deployed in association with the processing subsystem 12 to detect gaze direction of the eye(s) 44, and the processing subsystem 12 may utilize the detected gaze direction to detect a subject-initiated action. For example, the subject 40 may shift his/her gaze rapidly between the virtual object 92 (that appears as overlaid on the scene in the display image) and another portion of the display image 90 a certain number of times which can be indicative of a subject-initiated action. The processing subsystem 12 may be configured to compare the detected number of gaze shifts (detected by the eye tracker 70) to a threshold number (i.e., a set number) of gaze shifts, and may detect a subject-initiated action if the detected number of gaze shifts is within a margin (which may be zero) of the threshold number. The threshold number of gaze shifts and the margin may be pre-programmed into the processing subsystem 12.

As another example, the eye tracker 70 may detect blinks and other blink-related features (such as the length of blinks and the intervals between blinks), and the subject may initiate the action by blinking according to a set number of times and possibly also according to a set interval between the number of blinks and/or the length of the blinks. For example, the processing subsystem 12 may compare the detected number of blinks with a threshold number of blinks, and/or compare one more detected inter-blink intervals with a threshold inter-blink interval, and/or compare the length of one or more detected blinks with a threshold blink length. The processing subsystem 12 may detect a subject-initiated action if the detected number of blinks is within a margin (which may be zero) of the threshold number of blinks, and/or if the detected inter-blink intervals is within a margin (which may be zero) of the threshold inter-blink interval, and/or if the length of the detected blink(s) is/are within a margin (which may be zero) of the threshold blink length. The threshold number of blinks, the threshold inter-blink interval, and the threshold blink length, as well as the associated margins, may all be pre-programmed into the processing subsystem 12. As alluded to in previous sections of the present document, the eye tracker 70 can be advantageously used for providing blink information to the processing subsystem 12. The processing subsystem 12 can used this blink information to adjust the timing and/or control parameters, in particular the sample period and/or the non-display period to ensure that nerve impulses that are transmitted during blink periods are not used to form the perceived image.

In yet another example, the display device 60 may be implemented as a touchscreen display device that is configured to detect touch in response to touch input received from the subject 40 via a suitable input object such as one or more fingers of the subject or a stylus device. Here, the subject-initiated action can be detected by the display device 60, and can be relayed to the processing subsystem 12. Touchscreen display devices, and the methods and techniques for detecting touch actions initiated on touchscreen display devices, are well known in the art but will be briefly discussed here. Some touchscreen display devices utilize capacitive technology by employing capacitive touch screens, which are made up of multiple layers of glass and plastic, coated with a conductor material like indium tin oxide or copper. This conductive material responds when contacted by another electrical conductor, such as the bare finger or a stylus device. When the electrical conductor touches the display screen, an electric circuit is completed at the point where the conductor makes contact, changing the electrical charge at this location and resulting in a "touch" detection. Other touchscreen display devices utilize resistive technology by employing resistive touch screens. Here, a glass or hard plastic protective layer is blanketed by a resistive metallic layer that conducts charge. The protective layer and the metallic layer are separated by spacers such that when the protective layer is pressed on firmly (for example by the finger), the two layers make contact changing the electric charge at that location, which results in a "touch" detection.

When utilizing touchscreen displays, the processing subsystem 12 receives the "touch" detection, and identifies the data record that is associated with the location of the "touch" detection. This "touch" location is the spatial location of the display image that contains the virtual object.

It should be apparent to those skilled in the art that the above examples for detecting subject-initiated actions merely represent a sample of methods for detecting such actions, and other methods/techniques can be employed by the system 10 or by components associated with the system 10.

In response to detection of a subject-initiated action on the portion 94 of the display image 90 that contains at least part of the virtual object 92, the processing subsystem 12 identifies the correct data record (for example in a database) that is associated with the element or elements of image data of the display image 90 that is/are associated with the spatial location of the portion of the display image that contains at least part of the virtual object. As a result, when the subject 40 initiates an action on the portion 94, the image data element(s) of the display image that correspond to the portion 94 are identified by the processing subsystem 12, and the data record associated with the identified image data element(s) is also identified by the processing subsystem 12. The processing subsystem 12 may identify the correct data record based on the spatial location (coordinates) of the detected subject-initiated action, for example by identifying the data record that includes the spatial location, for example based on spatial location metadata in the data record(s).

Once the processing subsystem 12 identifies the correct data record, the attributes of or associated with the image data are also retrieved/identified by the processing subsystem 12. The attributes can include, for example, one or more responsive actions that can be initiated by the processing subsystem 12 in response to identifying the data record, the spatial location of the virtual object, the spatial location/coordinates in two- or three-dimensions of the portion 94 of the display image that contains the virtual object, characteristics or features of the virtual object, display image features or parameters such as the size (e.g., in pixels) of the display image and/or the size (e.g., in pixels) of the virtual object within the display image and/or the ratio between the size of the virtual object in the display image and the size of the display image (or vice versa).

According to certain embodiments, the position of the virtual object relative to the scene 80 in the display image 90 can be arbitrary, for example selected ad hoc by the processing subsystem 12 when the processing subsystem 12 generates the display image 90. In other embodiments, the position of the virtual object relative to the scene 80 in the display image 90 can be based on characteristics or features of the virtual object, such as the type of virtual object. For example, certain types of virtual objects may be displayed in certain regions of the display image, and other types of virtual objects may be displayed in other regions of the display image. In such embodiments, the position of virtual objects relative to a scene in the display image can be pre-programmed into the processing subsystem 12. For example, if the virtual object is associated with or representative of a real-world object, such as an electronic appliance, the processing subsystem 12 may display the virtual object in a position of the display image that is pleasing to the subject. Consider, for example, that the virtual object is an icon that represents a household appliance (e.g., microwave oven, dishwasher, laundry appliance such as a washing machine, dryer), the processing subsystem 12 may provide the image data of the virtual object to the display device 60 such the virtual object appears in a corner of the display image, or another eye-pleasing location in the display image.

In other embodiments, the position of the virtual object relative to the scene 80 in the display image 90 can be based on input data such as input from an eye tracking subsystem (e.g., eye tracker 70). For example, if the gaze direction of the eye(s) 44 is directed toward the bottom right corner of the display device 60, the eye tracker 70 can detect this gaze direction and provide a signal input to the processing subsystem 12 to display the virtual object in the bottom right corner of the display device 60.

In certain embodiments, the processing subsystem 12 can modify the display image, including the elements of the display image that correspond to the virtual object, so as to adjust display parameters of the display image. For example, the processing subsystem 12 may modify the display image to adjust/change the location of the virtual object within the display image. As another example, the processing subsystem 12 may modify the display image to increase or reduce the size of the virtual object (or other portions of the display image) relative to the other portions of the display image.

As mentioned, the processing subsystem 12 may initiate one or more responsive actions in response to identifying the data record. By way of one example, the one or more responsive actions can include activating and/or controlling a real-world object that the virtual object 92 is associated with or based upon. As mentioned above, real-world objects, can include, but are not limited to, a computer keyboard, computer mouse and the like, an interactive display screen, an aircraft cockpit, a HUD such as those which can be deployed in aircraft cockpits and motor vehicles (e.g., cars, buses, trains, trucks, heavy-duty vehicles and machinery such as constructions vehicles, excavation vehicles and the like, military vehicles, etc.), a control or operating panel of an aircraft or a motor vehicle (including the aforementioned types of vehicles), an electronic device/appliance such as a smartphone, tablet, digital radio receiver, speaker system, household appliance such as oven, microwave oven, dishwasher, laundry appliance (e.g., washing machine, dryer), and the like. Thus, for example, if the virtual object 92 is associated with a washing machine appliance, the one or more responsive actions can include, for example, controlling the washing machine to initiate a laundry cycle. In such an example, the virtual object 92 can be, for example, an icon representing the subject's washing machine, and interacting with the icon (by the subject, for example by pointing or gesturing to the icon, initiating a voice command, or any other invocation mechanism) can invoke a laundry cycle.

It is noted that in order to enable control of any electronic devices by the system 10 according to embodiments of the present disclosure, such electronic devices should be in electronic or data communication with the system 10 such that communication messages, including command-and-control messages and instructions, can be exchanged between the system 10 and the electronic device(s). In one set of non-limiting examples, the electronic devices are network-enabled devices, and communicate with the system 10 via a communication network. For example, the electronic devices can be fitted with a network device to become "smart" electronic devices, as is well-known in the art. Other of the electronic devices may be a pre-configured as network-enabled devices, for example pre-configured with wireless network communication hardware such as Bluetooth compliant hardware.

Figure 9:
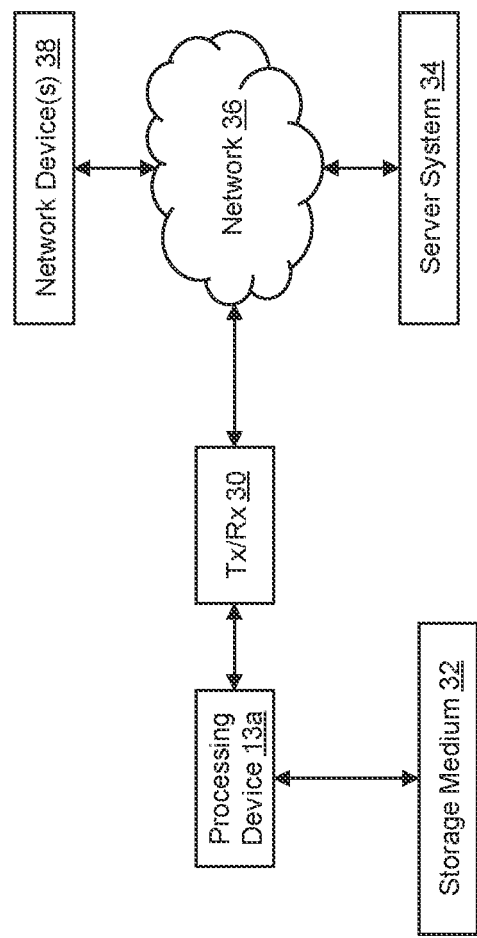
FIG. 9 is a schematic representation of a network system environment in which the system can operate according to embodiments of the invention

FIG. 9 schematically illustrates a networked system environment in which the system 10 can be deployed according to embodiments of the present disclosure. In the non-limiting embodiment illustrated in FIG. 9, the processing device 13a can be linked to a transceiver (Tx/Rx) unit 30 that provides a communication/network interface for transmitting/receiving data to/from (i.e., exchanging data with) one or more network devices 38 via a network 36 (which can be one or more communication networks, such as cellular networks, local area networks, the Internet, etc.). It is noted that FIG. 9 also shows an external storage medium 32 linked (e.g., electronically connected) to the processing device 13a, and a server system 34 (having one or more processors and one or more storage medium) communicatively coupled to the processing device 13a via the network 36. The external storage medium 32 can be used to store and provide to the processing device 13a various types of data, for example, image data representative of objects that are to be overlaid on the scene in the display image. The server system 34 can also be used to store and provide to the processing device 13a various types of data (similar to the external storage medium 32), and may also be configured to perform some (or all) of the processing functions of the processing device 13a. Thus, in certain embodiments, the processing subsystem 12 may include the server system 34.

It is noted that a given responsive action can be selected from a plurality of responsive actions, where each responsive action of the plurality of actions is associated with a corresponding data record of a plurality of data records, and where each data record of the plurality of data records is associated with a corresponding one or more elements of the image data of the display image 90 that is/are associated with a corresponding spatial location of the portion of the display image that contains at least part of the virtual object. As a result, for example, a given virtual object may have multiple locations, where each location is associated with a respective one or more image data elements and a respective responsive action. Consider as an example the virtual object being an icon representing the subject's washing machine. One area/location of the virtual object (icon) may correspond to a first responsive action, e.g., initiation of a laundry cycle, whereas another area/location of the virtual object (icon) may correspond to a second responsive action, e.g., termination of a laundry cycle.

As another non-limiting example, the one or more responsive actions can include displaying one or more new virtual objects to the subject as part of a display image, where each of the new virtual objects is associated with a corresponding responsive action. For example, the virtual object 92 may itself be a virtual computer keyboard, which appears to the subject 40 as a computer keyboard overlaid on the scene in the display image. The subject 40 can interact with the virtual keyboard to compose a message. For example, if the subject 40 wishes to compose the word "hello", the subject may initiate an action on the portion of the virtual keyboard containing the letter "h". Upon detection of this subject-initiated action, the processing subsystem 12 identifies the data record associated with the element or elements of image data of the display image 90 that is/are associated with the spatial location of the portion of the display image that contains the virtual letter "h". the subject 40 may then subsequently and sequentially initiate actions on the corresponding portions of the virtual keyboard containing the letters "e", "l", "l", and "o", and in response to each detected subject-initiated action, the processing subsystem 12 identifies the data record associated with the element or elements of image data of the display image 90 that is/are associated with the spatial location of the portion of the display image that contains the corresponding virtual letter.

As mentioned, a storage medium (e.g., memory or database) associated with the system 10, such as storage medium 16a and/or 16b, can be configured to store a set (i.e., plurality) of data records. According to certain embodiments, the plurality of data records is comprised of a plurality of subsets of data records, where each subset is associated with a different virtual object of a plurality of virtual objects. For example, the plurality of data records may include two subsets of data records, i.e., a first subset of data records and a second subset of data records. The first subset of data records may include two data records that are each associated with a first virtual object (e.g., a virtual icon corresponding to a household appliance), and the second subset of data records may include a single data record that is associated with a second virtual object (e.g., a virtual keyboard).

In certain scenarios it may be advantageous or beneficial for the subject to receive some type of feedback from the system 10 when the system 10 receives subject-initiated actions and/or when the system 10 initiates responsive actions. In certain non-limiting embodiments, the feedback can be provided by the system 10, for example by the processing subsystem 10, in the form of an alert or notification to the subject. For example, in response to an action being invoked on a virtual object in the display image, the processing subsystem 12 may provide an alert or notification to the subject, for example in the form of an aural alert (e.g., a chime or other sound). In another non-limiting example, the alert or notification can be in the form of a message, for example short message service (SMS) or other suitable text-based message, or in the form of an email. In yet another non-limiting example, the alert or notification can be a flag or marker applied to the identified data record, which can allow processing/handling, for example by the processing subsystem 12, at an appropriate time, for example a later time.

According to certain embodiments, the feedback may be physical feedback, which can be, for example, visual feedback or another type of sensory feedback that is initiated by the processing subsystem 12. For example, in one set of non-limiting embodiments, the feedback can be in the form of visual feedback within the display image itself. For example, in response to an action being invoked on a virtual object in the display image, the processing subsystem 12 may actuate the display device 60 to display an image or images which depicts an action corresponding to the invoked action. For example, continuing with the virtual keyboard example described above, if the subject 40 wishes to compose the word "hello", the processing subsystem 12 may provide to the display device 60 image data representative of an avatar or character typing on the virtual keyboard, such that the subject sees the avatar/character typing on the virtual keyboard in response to the subject initiating an action on the portion of the virtual keyboard containing the relevant letters.

In another set of non-limiting embodiments, the system 10 provides non-visual sensory feedback to the subject 40 using haptic technology. Haptic technology is one class of solutions for providing users/subjects with physical feedback, which create an experience of touch by applying forces, vibrations, or motions to the user/subject. Referring again to FIG. 1, in certain embodiments, for example, a haptic interface 75 can optionally be deployed in association with the processing subsystem 12 and the subject 40. The haptic interface 75 is configured to provide haptic feedback to the subject 40 in response to receiving input corresponding to the subject-initiated action and/or in response to the initiation of the responsive action(s). Haptic interface devices are well-known in the art, and can include, for example, gloves, watches, headsets, vests, or other wearable apparel, fitted with haptic feedback devices that produce vibrations or pressure (or other haptic feedback) that is sensed by the subject 40 by touch or feel. By way of one non-limiting example implementation, the haptic interface 75 can be implemented as a haptic glove that is configured to be worn on the hand of the subject 40 and that provides pressure or vibration feedback to one or more of the fingers on the hand that wears the haptic glove. In such an example, the subject 40 may initiate an action on a virtual object by "touching" the virtual object in the display image with his/her finger, and the haptic interface 75 may vibrate or apply pressure to the finger in response to the action initiated by the subject.

Although embodiments which support interaction with virtual objects and control of real-world objects have been described above within the context of the system 10 having a display device 60 which projects display images that are perceived images augmented to include one or more virtual objects, according to certain embodiments virtual object overlay and interaction may be accomplished without use of a display device.

According to one example embodiment, in order to present a virtual object to the subject as overlaid on a scene, the processing subsystem 12 can receive image data representative of an object, process that received image data (using the impulse-image mapping) to convert the image data to one or more nerve impulses that convey the image information, and then provide those nerve impulses to the visual processing region 43 of the brain 42 of the subject 40 while the subject 40 is viewing a real scene (e.g., scene 80) with his/her eye(s) 44, such that the subject 40 visually perceives the object (represented by the received image data) as a virtual object overlaid on the real scene viewed by the subject's eye(s) 44. Alternatively, according to another example embodiment, the processing subsystem 12 may convert collected nerve impulses, transmitted in response to the subject 40 viewing a real scene (e.g., scene 80), to image data (using the impulses-image mapping), and then modify this image data to include the object. The processing subsystem 12 can then convert the modified image data to nerve impulses and provide those nerve impulses to the visual processing region 43 of the brain 42 of the subject 40 while the subject 40 is viewing a real scene (e.g., scene 80) with his/her eye(s) 44, such that the subject 40 visually perceives the object (represented by the received image data) as a virtual object overlaid on the real scene viewed by the subject's eye(s) 44.

The processing subsystem 12 can then, as before, identify a data record associated with one or more elements of the image data that is representative of the object. These one or more elements of the image data that are associated with the identified data record are also associated with a spatial location of the virtual object as viewed by the object. As before, the data record preferably contains attributes of or associated with the image data, including, for example, one or more responsive actions that can be initiated by the processing subsystem 12 in response to identifying the data record, characteristics or features of the virtual object, display features or parameters such as the size of the virtual object in the subject's FOV, and the location that the virtual object is to be positioned within the subject's FOV. The processing subsystem 12 may then, as before, initiate a responsive action or actions that are associated with the virtual object(s) in response to identifying the data record.

The identification of the data record can, as before, be performed in response to detection of a subject-initiated action at or on the virtual object. In addition, embodiments lacking a display device may also employ a haptic interface to provide haptic feedback to the subject in response to subject-initiated actions and/or in response to the one or more responsive actions.

As mentioned, in human subjects, the visual processing region 43 is commonly referred to as the visual cortex. The visual processing region 43 is also commonly referred to as the visual cortex in many other non-human types of animals, including, for example, canine species, feline species, non-human primate species, and rodent species. In human subjects and many other vertebrates, the visual cortex is a part of the temporal lobe that processes visual information. In animal species (for example reptile species, bird species, non-mammal marine/aquatic species) that do not have a cerebral cortex or visual cortex, the term "visual processing region" refers to the equivalent portion or portions of the brain that performs visual processing. Thus, although the embodiments of the present invention are of particular use when applied within the context of human vision, embodiments of the present disclosure may be equally applicable to vision in non-human animal subjects, including, but not limited to, other primate species (e.g., monkeys, gorillas, etc.), canine species, feline species, reptile species, bird species, and non-mammal marine/aquatic species.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The block diagrams in the Figures illustrate the architecture, functionality, and operation of possible implementations of systems, methods and computer program products according to various embodiments of the present invention. In this regard, each block in the block diagrams may represent a module, segment, or portion of code, which comprises one or more executable instructions for implementing the specified logical function(s).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As used herein, the singular form "a", "an" and "the" include plural references unless the context clearly dictates otherwise. For example, reference to a single nerve can also refer to both nerves of a nerve pair. Furthermore, reference to both nerves of a nerve pair can also refer to a single nerve, unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, microprocessors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for use with a subject having a brain and at least one eye, the method comprising:
receiving, by a processing subsystem configured to be in communication with a visual processing region of the brain of the subject, signals associated with nerve impulses transmitted to the visual processing region in response to the subject viewing a scene with the at least one eye; and
processing, by the processing subsystem, the signals by applying to the signals at least one mapping having data that maps between nerve impulses and image data so as to produce generated image data that is representative of what the subject sees when viewing the scene with the at least one eye.

2. The method of claim 1, further comprising:
storing some or all of the generated image data in a storage medium associated with the processing subsystem.

3. The method of claim 1, further comprising:
sending some or all of the generated image data to one or more devices or systems communicatively coupled with the processing subsystem via one or more communication networks, wherein the one or more devices or systems include one or more of a server system, a computer system, a processing system, or a memory.

4. The method of claim 1, further comprising:
providing the image data to a display device for displaying an image corresponding to the generated image data.

5. The method of claim 1, further comprising:
modifying the generated image data to produce modified image data.

6. The method of claim 5, wherein the modifying includes incorporating additional image data into the generated image data, wherein the additional image data is retrieved by the processing subsystem from at least one of a storage medium that stores the additional image data, or an imaging device that generates the additional image data.

7. The method of claim 5, further comprising:
providing the modified image data to a display device for displaying an image corresponding to the modified image data.

8. The method of claim 1, further comprising:
generating a display image by combining the generated image data with object image data that is representative of an object such that the object appears as overlaid on the scene in the display image;
providing the display image to a display device; and
identifying a data record associated with one or more elements of display image data of the display image, the one or more elements of the display image data of the display image being associated with a spatial location of a portion of the display image that contains at least part of the object.

9. The method of claim 1, further comprising:
generating the at least one mapping.

10. The method of claim 1, further comprising: deploying an interfacing arrangement that places the processing subsystem in communication with the visual processing region.

11. The method of claim 10, wherein the interfacing arrangement is external to the subject.

12. The method of claim 1, wherein the processing subsystem includes a plurality of components, and wherein each component of the plurality of components of the processing subsystem is external to the subject.

13. A system for use with a subject having a brain and at least one eye, the system comprising:
a processing subsystem, including at least one processor communicatively coupled to a storage medium, configured for communicating with a visual processing region of the brain, the processing subsystem configured to:

receive signals associated with nerve impulses transmitted to the visual processing region in response to the subject viewing a scene with the at least one eye, and process the signals, by applying to the received signals at least one mapping having data that maps between nerve impulses and image data, so as to produce generated image data that is representative of what the subject sees when viewing the scene with the at least one eye.

14. The system of claim 13, further comprising: an interfacing arrangement for placing the processing subsystem in communication with the visual processing region.

15. The system of claim 14, wherein the interfacing arrangement is external to the subject.

16. The system of claim 13, wherein the processing subsystem includes a plurality of components, and wherein each component of the plurality of components of the processing subsystem is external to the subject.

17. The system of claim 13, wherein the processing subsystem is further configured to generate the at least one mapping.

18. The system of claim 13, wherein the processing subsystem is further configured to perform at least one operation on the generated image data, wherein the at least one operation is selected from the group consisting of:

i) storing some or all of the generated image data in a storage medium associated with the processing subsystem, ii) sending some or all of the generated image data to a server system communicatively coupled with the processing subsystem via one or more communication networks, iii) providing the image data to a display device for displaying an image corresponding to the generated image data, and iv) modifying the generated image data to generate modified image data.

19. A method for use with a subject having a brain, the method comprising:

processing, by a processing subsystem configured to be in communication with a visual processing region of the brain of the subject, scene image data that is representative of a scene by applying to the scene image data at least one mapping having data that maps between nerve impulses and image data so as to convert the scene image data to a sequence of nerve impulses; and providing the sequence of nerve impulses to the visual processing region of the brain of the subject such that the subject visually perceives the scene.

20. A system for use with a subject having a brain, the system comprising:

a processing subsystem, including at least one processor communicatively coupled to a storage medium, configured for communicating with a visual processing region of the brain of the subject, the processing subsystem configured to:

process scene image data that is representative of a scene by applying to the scene image data at least one mapping having data that maps between nerve impulses and image data so as to convert the scene image data to a sequence of nerve impulses, and provide the sequence of nerve impulses to the visual processing region of the brain of the subject such that the subject visually perceives the scene.

* * * * *